US009739770B2

(12) United States Patent
Su

(10) Patent No.: US 9,739,770 B2
(45) Date of Patent: Aug. 22, 2017

(54) LABEL-FREE DETECTION OF NANOPARTICLES AND BIOLOGICAL MOLECULES USING MICROTOROID OPTICAL RESONATORS

(71) Applicant: California Institute of Technology, Pasadena, CA (US)

(72) Inventor: Tsu-Te Judith Su, Pasadena, CA (US)

(*) Notice: Subject to any disclaimer, the term of this patent is extended or adjusted under 35 U.S.C. 154(b) by 0 days.

(21) Appl. No.: 14/658,063

(22) Filed: Mar. 13, 2015

(65) Prior Publication Data
US 2015/0301034 A1 Oct. 22, 2015

Related U.S. Application Data

(60) Provisional application No. 61/953,695, filed on Mar. 14, 2014.

(51) Int. Cl.
| | | |
|---|---|---|
| G01N 21/47 | (2006.01) |
| G01N 33/543 | (2006.01) |
| G01N 21/77 | (2006.01) |
| G01N 21/31 | (2006.01) |

(52) U.S. Cl.
CPC ....... *G01N 33/54373* (2013.01); *G01N 21/31* (2013.01); *G01N 21/7746* (2013.01); *G01N 33/54313* (2013.01)

(58) Field of Classification Search
CPC .............. G01N 21/31; G01N 21/7746; G01N 33/54313; G01N 33/54373
USPC .................................................. 356/432–446
See application file for complete search history.

(56) References Cited

U.S. PATENT DOCUMENTS

| | | |
|---|---|---|
| 7,236,664 B2 | 6/2007 | Armani et al. |
| 7,545,843 B2 | 6/2009 | Armani et al. |
| 7,781,217 B2 | 8/2010 | Armani et al. |
| 8,092,855 B2 | 1/2012 | Armani et al. |

(Continued)

OTHER PUBLICATIONS

Luchansky, M. S. & Bailey, R. C. High—Q Optical Sensors for Chemical and Biological Analysis. Anal. Chem. 84, 793-821, doi:10.1021/ac2029024 (2011).

(Continued)

*Primary Examiner* — Tri T Ton
(74) *Attorney, Agent, or Firm* — Strategy IP, a professional corp.

(57) ABSTRACT

Systems and methods are provided for detecting one or more particles such as individual unlabeled molecules or single nanoparticles. In examples described herein, optical energy is introduced into a microtoroid or other microcavity to generate an evanescent field. The microcavity has a functionalized outer surface that has been functionalized with a chemically or biologically active substance such as an antibody, antigen or protein. An indication of a particle bound to the functionalized outer surface of the microcavity is then detected based on a reactive interaction between the particle and the evanescent field while using frequency locking, balanced detection and various filtering techniques. The frequency locking, balanced detection and filtering techniques reduce the signal-to-noise ratio (SNR) of the detection system so that single nanoparticles (e.g. 2.5 nanometers (nm) in radius) and individual molecules (e.g. 15.5 kilo-Dalton (kDa) in size) can be detected in aqueous solution in some examples.

20 Claims, 19 Drawing Sheets

(56) References Cited

U.S. PATENT DOCUMENTS

| | | | |
|---|---|---|---|
| 8,094,987 | B2 | 1/2012 | Armani |
| 8,107,081 | B2 | 1/2012 | Armani et al. |
| 8,310,677 | B2 | 11/2012 | Armani et al. |
| 8,593,638 | B2 | 11/2013 | Lu et al. |
| 2002/0079453 | A1 | 6/2002 | Tapalian |
| 2004/0179573 | A1 | 9/2004 | Armani et al. |
| 2005/0111776 | A1 | 5/2005 | Martin et al. |
| 2007/0269901 | A1* | 11/2007 | Armani ............. G01N 21/7746 436/172 |
| 2010/0085573 | A1 | 4/2010 | Lu et al. |
| 2012/0120398 | A1 | 5/2012 | Armani et al. |

OTHER PUBLICATIONS

Vollmer, F. & Arnold, S. Whispering—gallery-mode biosensing: label-free detection down to single molecules. Nat. Methods 5, 591-596, doi:10.1038/nmeth.1221 (2008).
Rodriguez-Lorenzo, L., de la Rica, R., Álvarez-Puebla, R. A., Liz-Marzán, L. M. & Stevens, M. M. Plasmonic nanosensors with inverse sensitivity by means of enzyme-guided crystal growth. Nat Mater 11, 604-607, doi:http://www.nature.com/nmat/journal/v11/n7/abs/nmat3337.html#supplementary-information (2012).
Dantham, V. R., Holler, S., Kolchenko, V., Wan, Z. & Arnold, S. Taking whispering gallery-mode single virus detection and sizing to the limit. Appl Phys Lett 101, doi:Artn 043704 Doi 10.1063/1.4739473 (2012).
Dickson, R. M., Cubitt, A. B., Tsien, R. Y. & Moerner, W. E. On/off blinking and switching behaviour of single molecules of green fluorescent protein. Nature 388, 355-358, doi:10.1038/41048 (1997).
Rissin, D. M. et al. Single-molecule enzyme-linked immunosorbent assay detects serum proteins at subfemtomolar concentrations. Nat. Biotechnol. 28, 595-599, doi:10.1038/nbt.1641 (2010).
Wiesendanger, R. Scanning probe microscopy and spectroscopy : methods and applications. (Cambridge University Press, 1994), "Scanning Force Microscopy", p. 244.
Swaim, J. D., Knittel, J. & Bowen, W. P. Detection of nanoparticles with a frequency locked whispering gallery mode microresonator. Appl Phys Lett 102, — , doi:doi:http://dx.doi.org/10.1063/1.4804243 (2013).
Armani, D. K., Kippenberg, T. J., Spillane, S. M. & Vahala, K. J. Ultra-high—Q toroid microcavity on a chip. Nature 421, 925-928, doi:10.1038/nature01371 (2003).
Vahala, K. J. Optical microcavities. Nature 424, 839-846, doi:10.1038/nature01939 (2003).
Arnold, S., Khoshsima, M., Teraoka, I., Holler, S. & Vollmer, F. Shift of whispering—gallery modes in microspheres by protein adsorption. Opt. Lett. 28, 272-274 (2003).
Knight, A. Single molecule biology. (Elsevier/Academic, 2009). "Introduction: The "Single Molecule" Paradigm", pp. xvii-xxxv.
Lu, T. et al. High sensitivity nanoparticle detection using optical microcavities. Proc. Natl. Acad. Sci. U. S. A. 108, 5976-5979, doi:10.1073/pnas.1017962108 (2011).
He, L., Ozdemir, S. K., Zhu, J., Kim, W. & Yang, L. Detecting single viruses and nanoparticles using whispering gallery microlasers. Nat Nano 6, 428-432, doi:http://www.nature.com/nnano/journal/v6/n7/abs/nnano.2011.99.html#supplementary—information (2011).
Vollmer, F., Arnold, S. & Keng, D. Single virus detection from the reactive shift of a whispering—gallery mode. Proc. Natl. Acad. Sci. U. S. A. 105, 20701-20704, doi:10.1073/pnas.0808988106 (2008).
Zhu, J., Özdemir, a. K., He, L., Chen, D.-R. & Yang, L. Single virus and nanoparticle size spectrometry by whispering—gallery-mode microcavities. Opt. Express 19, 16195-16206, doi:10.1364/OE.19.016195 (2011).
Dantham, V. R. et al. Label-Free Detection of Single Protein Using a Nanoplasmonic—Photonic Hybrid Microcavity. Nano Lett. 13, 3347-3351, doi:10.1021/nl401633y (2013).
Kerssemakers, J. W. et al. Assembly dynamics of microtubules at molecular resolution. Nature 442, 709-712, doi:10.1038/nature04928 (2006).
Gamba, J. M., Flagan, R. C., Flagan, R. C. & California Institute of Technology. The Role of Transport Phenomena in Whispering Gallery Mode Optical Biosensor Performance Division of Chemistry and Chemical Engineering. in CIT theses 2012 1 online resource (xxiii, 139 leaves) ill. (California Institute of Technology Pasadena, Calif., 2012).
Ashkin, A., Dziedzic, J. M., Bjorkholm, J. E. & Chu, S. Observation of a single-beam gradient force optical trap for dielectric particles. Opt. Lett. 11, 288 (1986).
Arnold, S. et al. Whispering gallery mode carousel—a photonic mechanism for enhanced nanoparticle detection in biosensing. Opt. Express 17, 6230-6238, doi:10.1364/OE.17.006230 (2009).
Squires, T. M. Messinger, R. J. & Manalis, S. R. Making it stick: convection, reaction and diffusion in surfacebased biosensors. Nat Biotechnol 26, 417-426, doi:10.1038/nbt1388 (2008).
Gamba, J. M. & Flagan, R. C. Flow-enhanced transient response in whispering gallery mode biosensors. Applied Physics Letters 99, doi:Artn 253705.
Stern, E. et al. Label-free immunodetection with CMOS—compatible semiconducting nanowires. Nature 445, 519-522, doi:10.1038/nature05498 (2007).
Teng, J. et al. Athermal Silicon-on-insulator ring resonators by overlaying a polymer cladding on narrowed waveguides. Opt. Express 17, 14627-14633 (2009).
Knittel, et al., Back-scatter based whispering gallery mode sensing. Scientific Reports 3, Article No. 2974 doi:10.1038/srep02974.
Zhang et al. Terahertz real time focal plane imaging. Lasers and Electro-Optics Europe, 22-26 1-7, May 10-20, 2011. Retrieved from the Internet. <URL: http://ieeexplore.ieee.org/xpls/abs_all.jsp?arnunnber=5942523&tag=1 >. abstract.
Armani et al. Label-Free, Single-Molecule Detection with Optical Microcavities. Science 317 2, 3, 14, 16-18, 20 (5839): 783-787, 2007. Retrieved from the Internet. <URL: http://www.s.kanazawa-u.ac.jp/phys/biophys/References/Cantilevers/Cantiler-Sensor-Science-2007.pdf>. entire document.
Lee et al. Two-dimensional silicon photonic crystal based biosensing platform for protein 12 detection. Optics Express 15(8): 4530-45-5. 2007. [retrieved on May 12, 2015]. Retrieved from the Internet. <URL: http://www.ece.rochester.edu/projects/FauchetGroup/Publications/Files/Mindy%20Lee/OX%20published.pdf>. entire document.
Arnold, et al., Whispering gallery mode bio-sensor for label-free detection of single molecules: thermo-optic vs. reactive mechanism, Optics Express, Jan. 5, 2010, 281-287, vol. 18, No. 1, Optical Society of America, USA.
Vollmer, et al., Whispering-gallery-mode biosensing: label-free detection down to single molecules, Nature Methods, Jul. 2008, 591-596, vol. 5, No. 7, Nature Publishing Group, USA.

* cited by examiner

Example of Particle Detection using Frequency Locking and Balance Detection

300

302 — Functionalize an outer surface of a planar silica microtoroid or other toroidal microcavity using an efficacious amount of a chemically or biologically active substance such as an antibody, antigen or protein.

304 — Bind particle(s) to be detected -- such as one or more unlabeled molecules or nanoparticles having diameters of 1 - 200 nanometers (nm), especially 1 - 10 nm (e.g. less than 10 nm) and, e.g., 2 nm in size -- to the functionalized outer surface of a microcavity within an aqueous environment.

306 — Generate optical energy using a laser or other coherent optical source and route to a splitter to split the optical energy along first and second arms or paths of an optical fiber waveguide.

308 — Couple optical energy from the first arm of the waveguide into the microcavity (using, e.g., direct contact over-coupling) to circulate optical energy inside the microcavity to generate an evanescent field of sufficient strength to react with the bound particle(s) to cause a detectable shift in a wavelength of optical energy resonating in the microcavity while concurrently routing a portion of the optical energy from the laser along the second arm past the microcavity without any optical coupling.

310 — Route optical energy from the first and second arms of the waveguide into an auto-balanced photoreceiver to generate a balanced difference signal representative of a peak resonance wavelength associated with the bound particle(s), thereby providing an indication of the particle(s).

312 — Route the difference signal from the auto-balanced photoreceiver into a frequency locking system to lock a frequency of the laser to a frequency corresponding to the peak resonance wavelength associated with the particle(s) and then detect the particle(s) based on the peak resonance wavelength.

*FIG. 3*

LABEL-FREE DETECTION OF NANOPARTICLES AND BIOLOGICAL MOLECULES USING MICROTOROID OPTICAL RESONATORS

CROSS REFERENCE TO RELATED APPLICATIONS

This application claims the benefit under 35 U.S.C. 119 to U.S. Provisional Application Ser. No. 61/953,695, filed on Mar. 14, 2014, the contents of which are incorporated herein by reference.

STATEMENT REGARDING FEDERALLY SPONSORED RESEARCH

This invention was made with government support under National Research Service Award No. GM007616 awarded by the National Institutes of Health. The government has certain rights in the invention.

BACKGROUND

Field of the Disclosure

Aspects of the disclosure relate to resonant microcavity sensors.

Description of Related Art

Single-molecule detection is one of the fundamental challenges of modern biology. Detection techniques often use labels that can be expensive, difficult to produce, and for small analytes might perturb the molecular events being studied. Analyte size plays an important role in determining detectability. In this regard, highly sensitive biodetection is important for many applications such as high throughput drug discovery studies, as it can significantly reduce the amount of analyte needed and speed the assays. A variety of applications in medical diagnostics (e.g. detecting trace amounts of tumor specific antigens to monitor the re-occurrence of cancer) and public health (e.g. detecting bacteria or viruses) could benefit from improved speed and sensitivity. Methods such as fluorescent tagging and enzyme-linked immunosorbent assays (ELISA) are capable of highly sensitive biodetection down to the single molecule level. However, the labels can be expensive, difficult to produce and might perturb the molecular events being studied. If the sensitivity of label-free biosensing techniques can be advanced to the single-molecule level, fundamental studies may become more direct and decisive, permitting, for example, studies of molecular conformations and biosensing in general without the need for the fabrication of specific tags for each molecule of interest. Similar issues arise in the detection of other small objects or particles such as nanoparticles.

Accordingly, it would be desirable to provide improved systems, devices and methods for detecting, e.g., unlabeled biological molecules or nanoparticles and aspects of the disclosure are generally directed to that end.

SUMMARY

In an exemplary embodiment, a method for particle detection is provided including: introducing electromagnetic energy into a microcavity to generate an evanescent field extending beyond an outer surface of the microcavity; and detecting an indication of a particle bound to the functionalized outer surface of the microcavity based on a reactive interaction between the particle and the evanescent field using frequency locking and balanced detection.

In another exemplary embodiment, a system is provided for particle detection including: an input system operative to introduce electromagnetic energy into a microcavity to generate an evanescent field extending beyond an outer surface of the microcavity; and a frequency-locked and balanced detector operative to detect an indication of a particle bound to the functionalized outer surface of the microcavity based on a reactive interaction between the particle and the evanescent field using frequency locking and balanced detection.

In an illustrative embodiment, the particle or particles to be detected comprises one or more unlabeled molecules or nanoparticles. In some examples, the particle is a single unlabeled molecule. The electromagnetic energy is optical energy received from a coherent light source, which is introduced into the microcavity by coupling the optical energy into the microcavity from a waveguide to circulate energy inside the microcavity to generate an evanescent field of sufficient strength to react with one or more of the particles to cause a detectable shift in a wavelength of optical energy resonating in the microcavity. Prior to coupling the optical energy into the microcavity, the energy may be split from the coherent light source onto first and second waveguide arms to couple a first portion of optical energy into the microcavity using the first arm of the waveguide while routing a second portion of optical energy along the second arm of the waveguide without microcavity coupling. A balanced receiver may be employed to receive the optical energy along the first and second arms of the waveguide for generating a balanced difference signal representative of a peak resonance wavelength associated with zero, one, or more particles to thereby provide an indication of the presence of the number of particles bound to the microcavity. A frequency-locking system may be employed to receive an output of the balanced receiver and lock a frequency of the coherent light source to a frequency corresponding to the peak resonance wavelength associated with one or more of the particles. The use of frequency locking and balanced detection may serve to reduce a signal-to-noise ratio (SNR) associated with particle detection. Digital filtering may also be performed including, e.g., one or more of Fourier filtering and median filtering.

Still further, in the illustrative embodiment, the microcavity is a planar microtoroid formed of silica and immersed in an aqueous environment during particle detection. The microtoroid has a Q value sufficient to allow detection of an indication of individual unlabeled molecules bound to the functionalized outer surface based on a wavelength shift of optical energy resonating in the microcavity. In some examples, the microtoroid has a Q value less than $10^6$. The outer surface of the microtoroid may be functionalized with one or more of a chemically or biologically active substance such as an antibody, antigen or protein.

In yet another exemplary embodiment, a method for unlabeled molecule detection is provided that includes: introducing electromagnetic energy into a microcavity to generate an evanescent field extending beyond an outer surface of the microcavity; and detecting an indication of an unlabeled molecule bound to the functionalized outer surface of the microcavity based on a reactive interaction between the unlabeled molecule and the evanescent field.

System and method examples are described in detail below.

BRIEF DESCRIPTION OF THE DRAWINGS

Referring now to the drawings in which like reference numbers represent corresponding parts throughout and in which:

FIG. 3 illustrates an exemplary method for detecting particles using a microcavity in accordance with the general method of FIG. 1 wherein frequency locking and balanced detection are employed;

DETAILED DESCRIPTION OF ILLUSTRATED EMBODIMENTS

Figure 1:
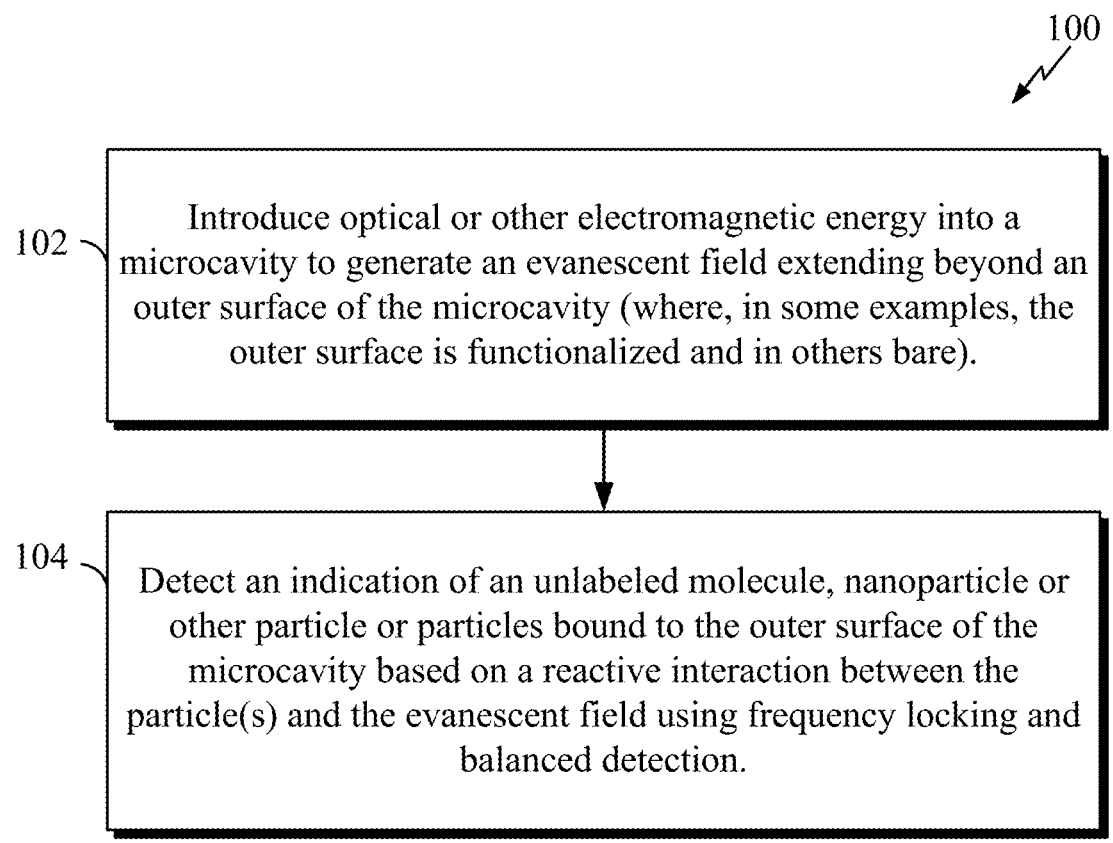
FIG. 1 provides an overview of methods for detecting an indication of particles using a microcavity while exploiting frequency locking and balanced detection.

In the following descriptions, specific details are given to provide a thorough understanding of the various aspects of the disclosure. However, it will be understood by one of ordinary skill in the art that the aspects may be practiced without these specific details. The word "exemplary" is used herein to mean "serving as an example, instance, or illustration." Any implementation or aspect described herein as "exemplary" is not necessarily to be construed as preferred or advantageous over other aspects of the disclosure. Likewise, the term "aspects" does not require that all aspects of the disclosure include the discussed feature, advantage or mode of operation.

Overview of Detection Techniques and Results

Systems and methods are described herein where frequency locking, balanced detection and filtering techniques are used to improve the SNR of microtoroid optical resonators so that single nanoparticles (e.g. 2.5 nanometers (nm) in radius) and individual molecules (e.g. 15.5 kilo-Dalton (kDa) in size) can be detected in aqueous solution in at least some examples, thereby bringing detectors to the size limits appropriate for detecting key macromolecules of a cell. Experiments are also described, covering several orders of magnitude of particle radius (100 nm to 2 nm), that substantially agree with "reactive" model predictions for the frequency shift of the resonator upon particle binding. This tends to confirm that the main contribution of the frequency shift for the resonator upon particle binding is an increase in the effective path length due to part of the evanescent field coupling into the adsorbed particle. These results may enable many applications, including more sensitive medical diagnostics and fundamental studies of single receptor-ligand and protein-protein interactions in real time or substantially in real time.

Frequency locking feedback control has been used in applications such as scanning tunneling microscopy to maintain tip-surface separation. In the realm of particle detection, frequency locking feedback control appears to have been applied to relatively large nanoparticles (39 nm×10 nm nanorods) but not biological molecules. See, Swaim et al. "Detection of nanoparticles with a frequency locked whispering gallery mode microresonator." Applied Physics Letters 102, 183106 (2013). Herein, frequency locking is applied to resonant biodetection along with balanced detection while using optical resonators to achieve a sensitivity that enables detection of a wide range of nanoscale objects ranging from nanoparticles with radii from, e.g., 100 nm down to 2.5 nm to exosomes, ribosomes, and single protein molecules (e.g., 160 kDa and 15.5 kDa). Accordingly, techniques described herein may be applied, for example, to the detection of nanoparticles less than 10 nm in size and, e.g., in the range of 1 nm to 9 nm in size. Still further, techniques described herein may be applied, for example, to the detection of molecules less than 200 kDa and, e.g. in the range of 10 kDa to 200 kDa.

Optical resonators such as microtoroids work on the principle of total internal reflection. Light circulates within these (often glass) devices generating an evanescent field that interacts multiple times with analytes that bind to the surface of the resonator. The long photon confinement time (on order of tens of nanoseconds) of the microtoroid can make it an extremely sensitive detector with a theoretical limit of detection down to single molecules. This enables obtaining the statistics of unitary events as opposed to merely looking at an ensemble average. Optical resonators have a further advantage that, because their surface can be functionalized, they do not require fluorescent tags, thus eliminating artifacts due to bleaching, blinking and tag interference. Moreover, because optical resonators can obtain data in the microsecond time regime continuously over several seconds or more, they have the potential to bridge a variety of time and length scales. In addition, optical resonators have a large (~300 $\mu m^2$) capture area thus making particle detection events more likely to occur than with nanodevices such as nanowires or nano-electrical-mechanical cantilevers. Currently, due to SNR limitations, the smallest particle radius a bare optical resonator has been shown to detect is 12.5 nm in aqueous solution and 10 nm in air. See, for example, Lu et al., "High sensitivity nanoparticle detection using optical microcavities." Proc. Natl. Acad. Sci. U.S.A. 108, 5976-5979. In terms of single-particle biological detection, optical resonators such as microspheres and microtoroids have been used to detect individual virus particles (~100 nm) without the use of labels. Microspheres have been coupled to 70 nm radius gold nanoshells to form a hybrid system capable of detecting single bovine serum albumin (BSA) molecules (e.g. 66 kDa).

The exemplary systems and methods described herein exploit a Frequency Locked Optical Whispering Evanescent Resonator (FLOWER) that can improve the detection capabilities of optical resonators in general, including hybrid systems. Both theory and finite element electromagnetic computations (using, e.g., COMSOL™) indicate that for a microtoroid to detect particles of comparable size to single protein molecules (2.5 nm radius, M~36 kDa), the sensor should be able to resolve a wavelength shift less than 0.006 femtometer (fm), which is ~80 times smaller than the approximate wavelength shift seen for detecting particles with a radius of 12.5 nm in an aqueous solution. To detect such small wavelength shifts, exemplary systems and methods described herein use frequency locking in combination with balanced detection and certain filtering techniques to reduce the noise level to, e.g., $9.6 \times 10^{-4}$ fm over one-millisecond intervals. A step-finding algorithm or procedure may be used to locate binding events. See, e.g., Kerssemakers et al., "Assembly dynamics of microtubules at molecular resolution." Nature 442, 709-712.

The frequency locking approach described herein has advantages over prior scanning systems that continually sweep back and forth over a large frequency range (e.g., $3.1 \times 10^4$ fm), only occasionally matching resonance. In contrast, the FLOWER system, in at least some examples, directly tracks the resonant wavelength location within a narrow and adaptively varied frequency range with a fixed length of 19 fm. Thus FLOWER tracks discrete fluctuations in the signal more accurately and quickly, permitting slight and transient events to be detected. To isolate a signal, FLOWER computationally filters out known sources of noise such as 60 Hz electronic line noise and applies a median filter to the data. As noted, frequency locking has been previously used in conjunction with microtoroid optical resonators, although for the detection of larger nanoparticles (39 nm×10 nm nanorods). FLOWER is capable of detecting significantly smaller particles (r~2 nm) by exploiting a number of advances, including the use of balanced photodetectors, direct laser frequency modulation instead of external phase modulation, a lower dither frequency of 2 kHz versus 200 MHz, the use of 24-bit data acquisition cards, as well as nonlinear post-processing filtering routines.

To characterize the FLOWER system, polystyrene latex nanoparticles were detected over a range of radii, and 2.5 nm silica nanoparticles at picomolar concentrations. Detection was performed in water using microtoroids approximately 80-100 μm in diameter, with selected resonant peaks having loaded quality factors (Q) of ~$1 \times 10^5$-$5 \times 10^6$ in water with an input power of 9.3-100 μW at 633 nm. These moderate Q-factors are chiefly a result of the optical fiber being positioned in direct contact with the microtoroid in the over-coupled regime. This procedure was chosen, at least in part, to minimize noise due to the optical fiber fluctuating against the toroid during the experiment. Furthermore, experiments were performed under conditions where fluid was injected toward the toroid with enough sample volume to completely exchange the liquid in the sample chamber three times, before stopping, waiting thirty seconds, and then recording data. This approach was found to mitigate noise from the optical fiber fluctuating against the toroid that occurs when a continuous injection is used.

Experimental results show that after implementing frequency locking, individual detection events appear much more cleanly and that the change in resonant wavelength of the microtoroid upon particle binding is proportional to particle volume. The theoretical basis for this result is discussed below. To further establish that detection of single 2.5 nm silica particles is achieved, experiments were performed under three different concentrations (0.2, 1, and 5 pM) to record the step amplitude and dwell time (time between steps) distributions. As expected, as the particle concentration increased, the mean step amplitude remained constant, as the mean particle diameter did not change. Furthermore, the amplitude of the steps obtained was found to be in agreement with that predicted by theory. These experiments are discussed in greater detail below.

It is noted that, in contrast to the experiments with 10-100 nm nanoparticles that show few down-steps, in the 2.5 nm experiments, a significant number of down-steps were observed, although there are still more up-steps than down-steps overall. This is consistent with other reported particle detection work using the microtoroid, where, as the particle diameter decreases, particle desorption becomes more frequent. This was expected both from the decreased surface area of interaction and also because optical trapping forces (in this case from the resonator field) decrease with particle size. The dwell times associated with the 2.5 nm detection experiments clearly decrease with increasing concentration. Assuming that the adsorption of particles follows a Poisson process, the dwell times should follow an exponential distribution, which was observed. As described below, exponential fits to the function were performed and the rate parameter was recovered to be 1500, 2400, 2700 steps/second for the 0.2, 1, and 5 pM cases, respectively, demonstrating that dwell times scale with concentration. These values indicate an offset at 0 pM, suggesting impurities in the background solution.

As with many nano- or micro-sensors, dwell times observed with FLOWER are shorter than would be expected from diffusion alone. Recent work by Arnold, et al. (described in "Whispering Gallery Mode Carousel—a Photonic Mechanism for Enhanced Nanoparticle Detection in Biosensing." Opt. Express 17, 6230-6238 2009) has shown that microspherical optical resonators generate optical trapping forces that cause significantly enhanced (100×) nanoparticle transport velocities. It is anticipated this effect will be even greater with the FLOWER system as it is (in at least some examples) always on resonance as opposed to sweeping past resonance, thus increasing the amount of circulating power the devices experience. In addition, with the configuration of the FLOWER microtoroid setup and with injection directly towards the toroid, convection plays a significant role in the flow around the toroid. This can significantly increase the particle encounter rate, particularly for smaller particle sizes and is consistent with the binding rates from nanowire experiments which report saturation from the binding of thousands of molecules within seconds at similar concentrations. A scaling argument, presented below, may help to elucidate this phenomena.

To demonstrate the use of FLOWER for biological applications, bioparticles were detected ranging in equivalent radii from 25 nm to <2.5 nm (molecular weight, 15.5 kDa). In particular, exosomes were detected from human mesenchymal stem cells, yeast ribosomes, mouse immunoglobulin G, and human interleukin-2. For the specific detection of particles in complex solutions, as was the case for the experiments involving exosomes and human interleukin-2, antibodies were attached to the surface of the toroid surface using a silane linker, discussed below. Experiments involving yeast ribosomes and mouse immunoglobulin G were performed in purified solutions without antibody functionalization of the surface of the toroid.

Results over a range of sizes, discussed below, show discrete, step-like, binding events with a step amplitude that corresponds well with the 'reactive' model prediction, indicating that FLOWER detects single particles and not clusters. As with the nanoparticle detection data, the time delay between bioparticle binding events follows an exponential distribution. Unbinding steps in the IL-2 experiment, also discussed below, are likely due to non-specific adsorption associated with the IL-2 binding to non-functionalized regions of the toroid; X-ray photoelectron spectroscopy (XPS) revealed that the linker only covered ~3% of the available surface.

Thus, in various experiments, nanoparticles were detected over a large range of sizes to validate the applicability of FLOWER to bio-detection using exosomes, ribosomes, mouse immunoglobulin G, and human interleukin-2. The results support the 'reactive' model that suggests that the main contribution of the frequency shift upon particle binding is caused by the energy required for the reactive (evanescent) field to polarize the particle. With theory and experiment in good agreement, FLOWER provides a system, method, apparatus and/or means for detecting single molecules in solution, thus potentially allowing for optically estimating the mass of single molecules in solution, performing fundamental studies in biophysics, and developing applications such as high throughput drug discovery and early detection of diseases.

Exemplary Detection Systems and Methods

FIG. 1 provides an overview of an exemplary method 100 for particle detection using a microcavity while exploiting frequency locking and balanced detection. Briefly, at 102, optical or other electromagnetic energy is introduced into a microcavity to generate an evanescent field extending beyond an outer surface of the microcavity (where, in some examples, the outer surface is functionalized and in others bare). In many of the specific examples described herein, the outer surface is functionalized, though that is not necessary in all cases and hence a bare microcavity might instead be employed (for at least some types of particle detection). At 104, an indication of an unlabeled molecule, nanoparticle or other particle or particles bound to the functionalized outer surface of the microcavity is detected based on a reactive interaction between the particle(s) and the evanescent field using frequency locking and balanced detection. Herein, note that the term "particle" generally refers to a minute quantity or fragment of matter and can comprise one or more particles or sub-particles, including individual molecules or groups or molecules. Typically, the particles are nanoscale particles, i.e. objects having a size on the order of nanometers. In some cases, these may be referred to as sub-micron particles or submicroscopic particles.

Figure 2:
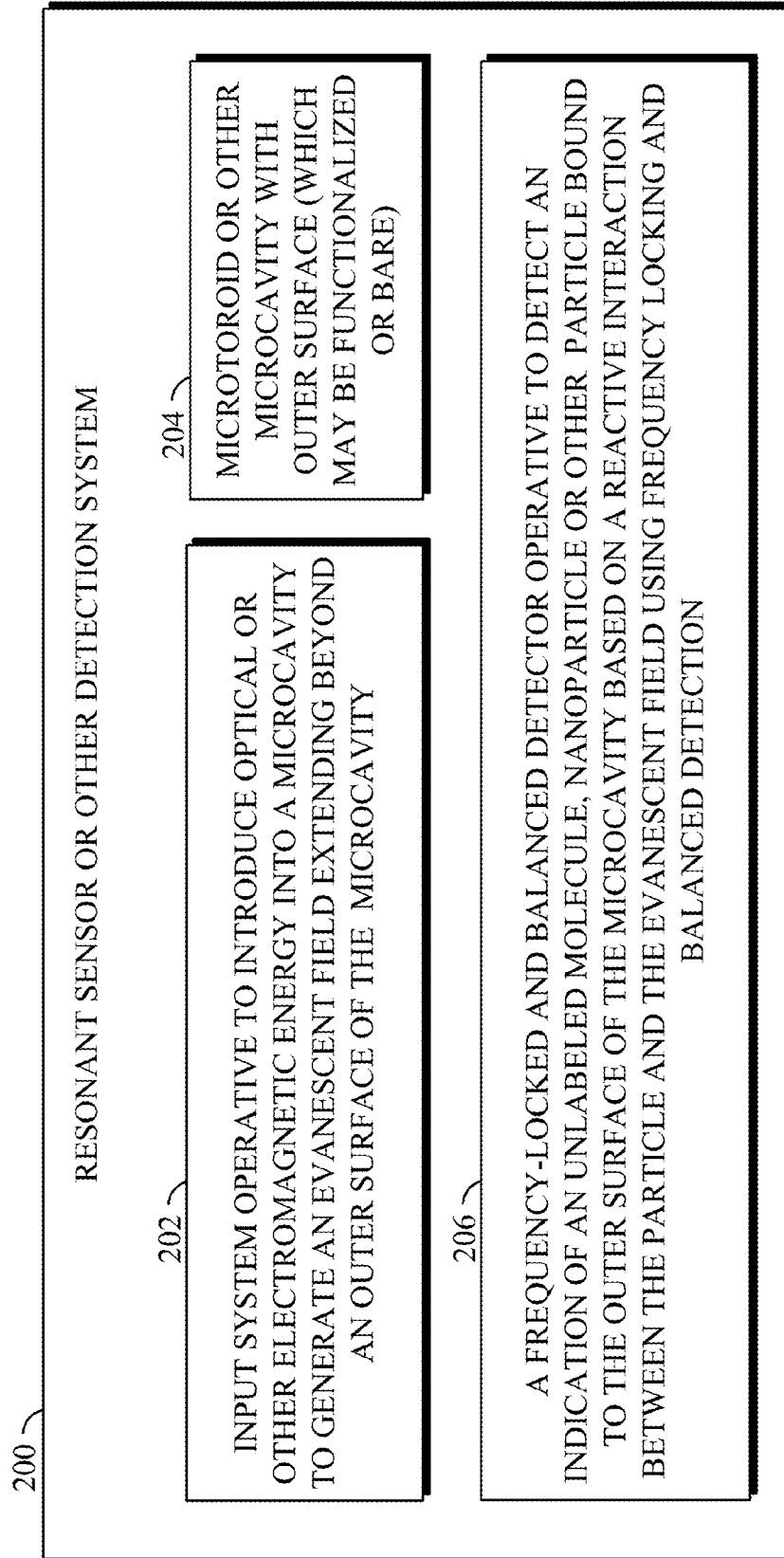
FIG. 2 provides an overview of a system operative to detect particles using a microcavity while exploiting frequency locking and balanced detection.

FIG. 2 provides an overview of the Frequency Locked Optical Whispering Evanescent Resonator (FLOWER) system that provides a resonant sensor or other detection system 200 for particle detection using a microcavity while exploiting frequency locking and balanced detection. Briefly, the system includes an input system 202 operative to introduce optical or other electromagnetic energy into a microcavity to generate an evanescent field extending beyond an outer surface of the microcavity and a microtoroid or other microcavity 204 (which may be functionalized or bare). A frequency-locked and balanced detector 206 is operative to detect an indication of a particle bound to the outer surface of the microcavity 204 based on a reactive interaction between the particle and the evanescent field using frequency locking and balanced detection.

FIG. 3 illustrates an exemplary method 300 for detecting particles using a microcavity in accordance with the general method of FIG. 1 wherein frequency locking and balanced detection are employed. At 302, an outer surface of a planar silica microtoroid or other toroid-shaped microcavity is functionalized using an efficacious amount of a chemically or biologically active substance such as an antibody, antigen or protein. That is, an efficacious amount of the active substance is applied to the outer surface of the microtoroid or to other suitable surfaces of the microtoroid. In other examples, the microcavity may have a different shape other than a toroid shape. At 304, one or more particle(s) to be detected—such as one or more unlabeled molecules or nanoparticles having diameters of 1-200 nanometers (nm), especially 1-10 nm (e.g. less than 10 nm) and, e.g., 2 nm in size—are bound to the functionalized outer surface of a microcavity within an aqueous environment. Hence, techniques described herein may be applied, for example, to the detection of nanoparticles in the range of 1 nm to 9 nm in size. However, in other examples, detection may be applied to larger particles, such as those up to 200 nm, i.e. in the range of 10-200 nm. Still further, techniques described herein may be applied, for example, to the detection of molecules less than 200 kDa and, e.g. in the range of 10 kDa to 200 kDa.

At 306, optical energy is generated using a laser or other coherent optical source and is routed to a splitter to split the optical energy along first and second arms or paths of an optical fiber waveguide. At 308, optical energy is coupled from the first arm of the waveguide into the microcavity (using, e.g., direct contact over-coupling) to circulate optical energy inside the microcavity to generate an evanescent field of sufficient strength to react with the bound particle(s) to cause a detectable shift in a wavelength of optical energy resonating in the microcavity while concurrently or simultaneously routing a portion of the optical energy from the laser along the second arm past the microcavity without any optical coupling. At 310, optical energy from the first and second arms of the waveguide are routed into an auto-balanced photoreceiver to generate a balanced difference signal representative of a peak resonance wavelength associated with the bound particle or particles, thereby providing an indication of the presence of the particle(s). At 312, the difference signal is routed from the auto-balanced photoreceiver into a frequency locking system to lock a frequency of the laser to a frequency corresponding to the peak resonance wavelength associated with the particle(s) and then the particle(s) are detected based on the peak resonance wavelength. More specifically, as already explained, detection may exploit a step-finding algorithm or procedure to locate or identify binding events so as to detect or identify the particle(s).

Figure 4:
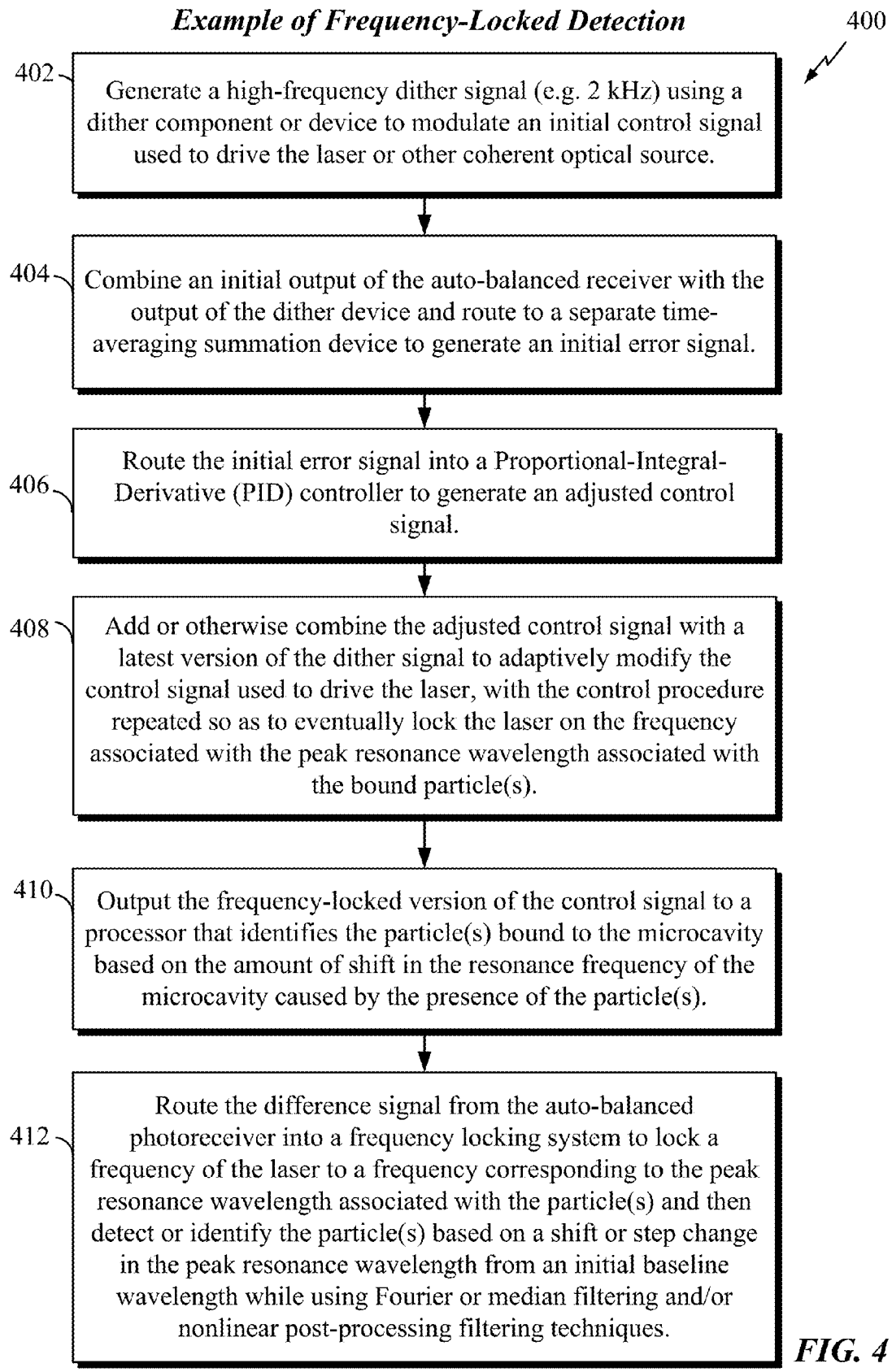
FIG. 4 illustrates an exemplary frequency-locking detection method in accordance with the example of FIG. 3.

FIG. 4 illustrates an exemplary method 400 for frequency locked detection of particles that may be used along with the method of FIG. 3 (such as to implement block 312) to achieve frequency locking and balanced detection. At 402, a high-frequency dither signal is generated using a dither component or device to modulate an initial control signal used to drive the laser or other coherent optical source. At 404, the initial output of the auto-balanced receiver is combined with the output of the dither device and route to a separate time-averaging summation device to generate an initial error signal. At 406, the initial error signal is routed into a Proportional-Integral-Derivative (PID) controller to generate an adjusted control signal. At 408, the adjusted control signal is added or otherwise combined with a latest version of the dither signal to adaptively modify the control signal used to drive the laser, with the control procedure repeated so as to eventually lock the laser on the frequency associated with the peak resonance wavelength associated with the bound particle or particles. At 410, the output of the frequency-locked version of the control signal is output to a processor that identifies or otherwise detects the particle or particles bound to the microcavity based on the amount of shift in the resonance frequency of the microcavity caused by the presence of the particle(s). At 412, the difference signal is routed from the auto-balanced photoreceiver into a frequency locking system to lock a frequency of the laser to a frequency corresponding to the peak resonance wavelength associated with the particle or particles and then the particle(s) are detected or identified based on a shift or step change in the peak resonance wavelength from an initial baseline wavelength while using Fourier or median filtering and/or nonlinear post-processing filtering techniques. The detection may be performed by a computing device that receives the latest version of the feedback control signal used to control the laser and which thereby provides an indication of the resonance wavelength.

Figure 5:
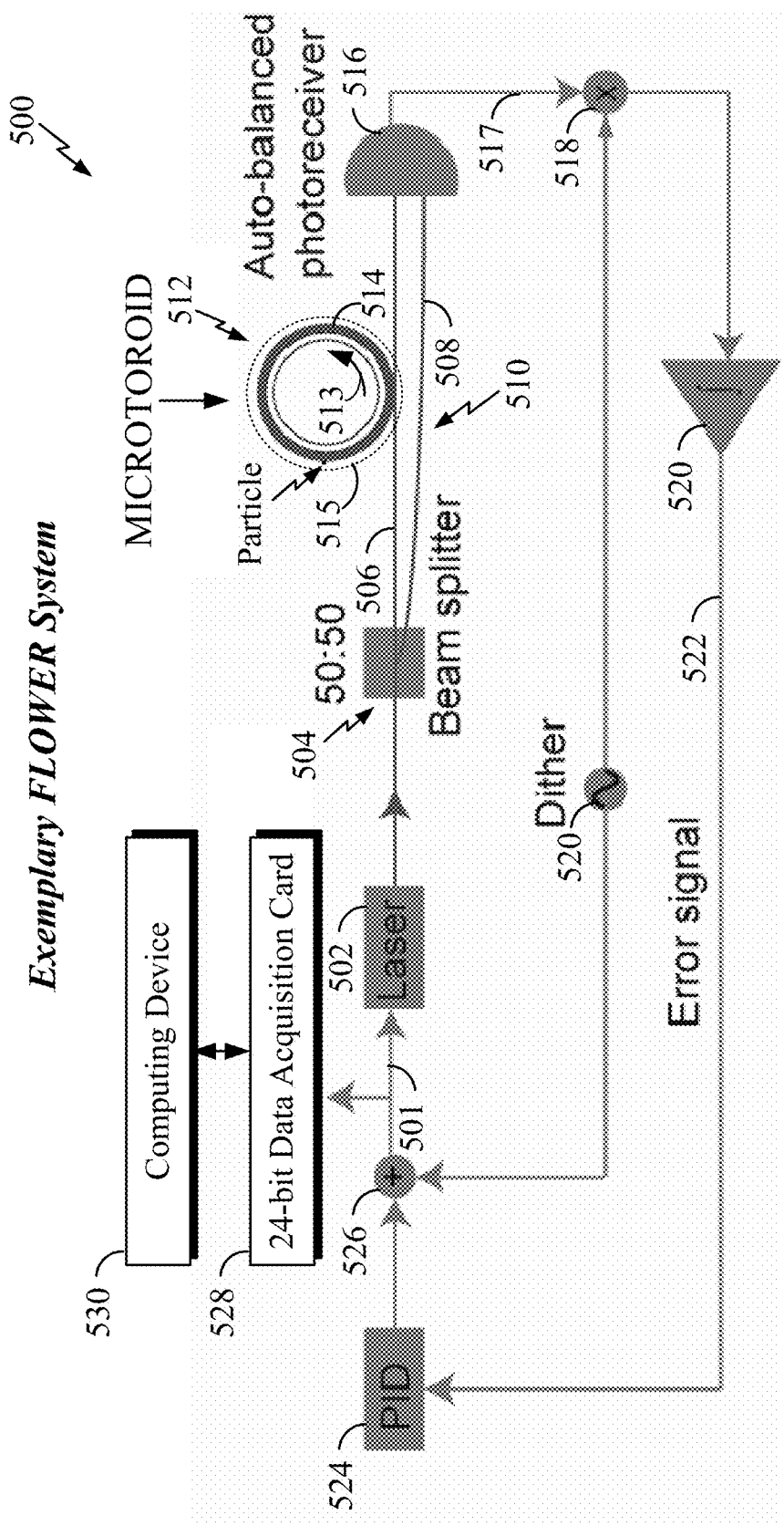
FIG. 5 illustrates further details of an exemplary frequency-locking and balanced detection system in accordance with the examples of FIGS. 3 and 4.

FIG. 5 illustrates an exemplary FLOWER system 500 operative to detect one or more particles using a microcavity while exploiting frequency locking and balanced detection, as discussed in connection with FIGS. 3 and 4. A laser 502 or other coherent light source generates optical energy at a frequency or wavelength set by a control signal 501. The optical energy is fed or routed into a 50/50 beam splitter 504, which splits the optical energy along first and second arms 506 and 508 of a waveguide 510 (which may be include one or more optic fibers or portions thereof). Arm 506 is coupled (via direct contact over-coupling) into microtoroid 512 (~90 microns in diameter) to circulate optical energy 513 inside the microtoroid to generate an evanescent field 515 (shown in dashed lines) of sufficient strength to react with at least one particle bound to a functionalized outer surface 514 of the microtoroid to cause a detectable shift in a wavelength of optical energy resonating in the microtoroid. Concurrently or simultaneously, a portion of the optical energy from laser 504 is routed along second arm 508 past the microtoroid without any significant optical coupling into the microtoroid.

Distal ends of waveguide arms 506 and 508 are coupled into an auto-balanced photoreceiver 516, which generates a balanced difference signal 517. Note that, at resonance, light emerging from the microtoroid along arm 506 destructively interferes with light along arm 508, causing a dip in the transmission (peak in absorption) vs. light wavelength. The difference signal 517 is routed to a multiplier 518, which also receives a dither signal from a dither component or device 520 and multiplies or otherwise combines the signals, which are then fed into a time-averaging integrator or summation device or component 520 to generate an error signal 522. Error signal 522 is then fed or routed into a PID 524 and its output is combined using an adder 526 to yield an adjusted control signal 501, which modulates the laser 502.

In this manner, a small high-frequency dither is used to modulate the driving laser frequency. When multiplied by the microtoroid output and time-averaged, the dither signal generates an error signal whose amplitude is proportional to the difference between the current laser frequency and the resonant frequency of the microtoroid. As noted, the error signal is sent to a PID controller whose output is used to modulate the laser frequency, thus completing the feedback loop. A 24-bit data acquisition card 528 records frequency shifts so that a computing device 530 can detect the particle or particles based on the amount of shift using techniques described in greater detail below. Hence, in this example, particles can be detected based on the control signal 501 used to control the laser. In other examples, other signals generated by the system can instead be used. For example, error signal 522 can instead be measured or otherwise tracked for use in detecting particles.

Figure 6:
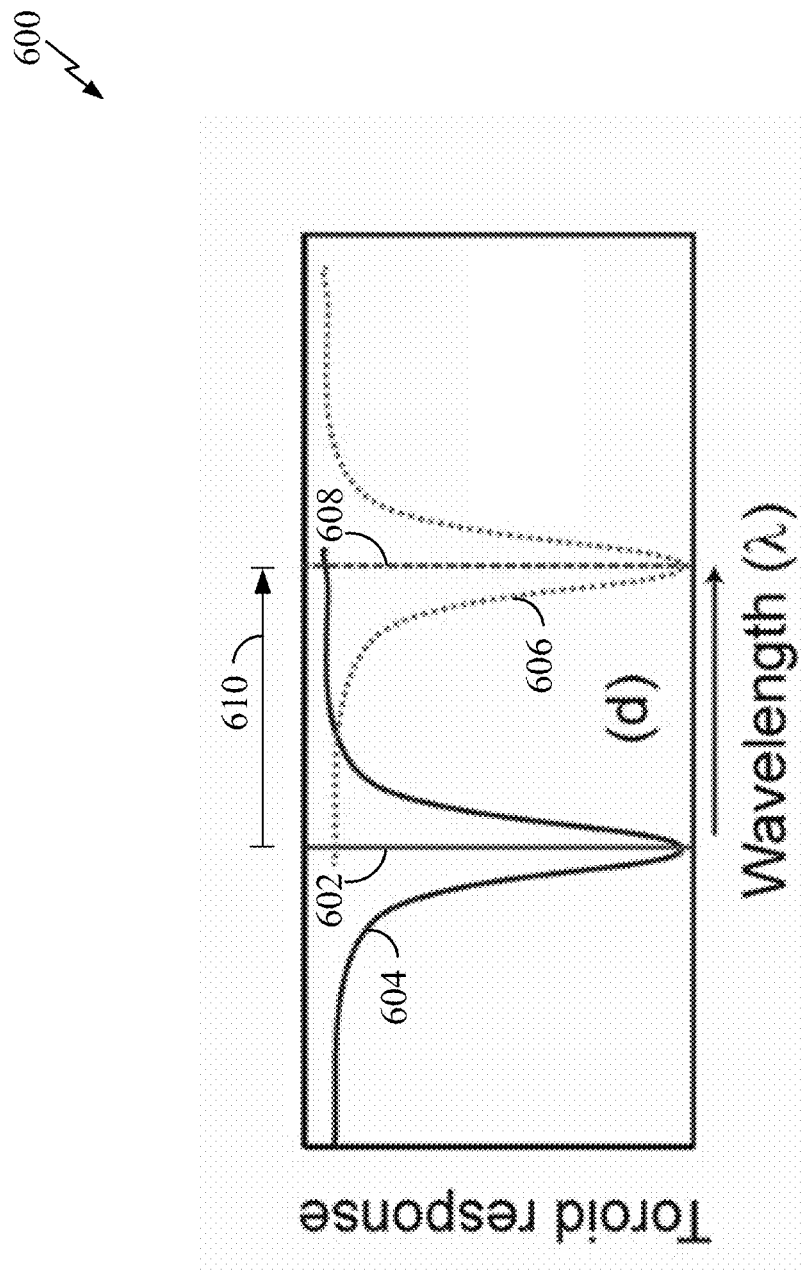
FIG. 6 is a graph illustrates a wavelength shift exploited by the exemplary frequency-locking and balanced detection system of FIG. 5 to detect a particle.

FIG. 6 provides a graph 600 illustrating the aforementioned shift. A laser frequency 602 is locked to a peak of a resonance frequency curve 604 of the microtoroid. As one or more particles bind to the microtoroid within the evanescent field, the resonant frequency curve of the microtoroid shifts to a new curve 606. The FLOWER system measures the control signal needed to keep the laser locked to the peak 608 of the new resonance frequency curve 606 and, from that control signal, the system determines the shift 610 from the initial frequency to the shifted frequency. The identity of the particle is then determined or otherwise detected based on the value of the shift, with different particles having different known shift values, or from various step values associated with those shifts. For example, a lookup table may be employed that provides shift values or step values associated with various known particles or molecules to permit a computing device to identify the particle or molecule. As already explained, frequency locking and balanced detection help to improve the SNR of system to allow more reliable detection of particles such as unlabeled molecules and nanoparticles.

Figure 7:
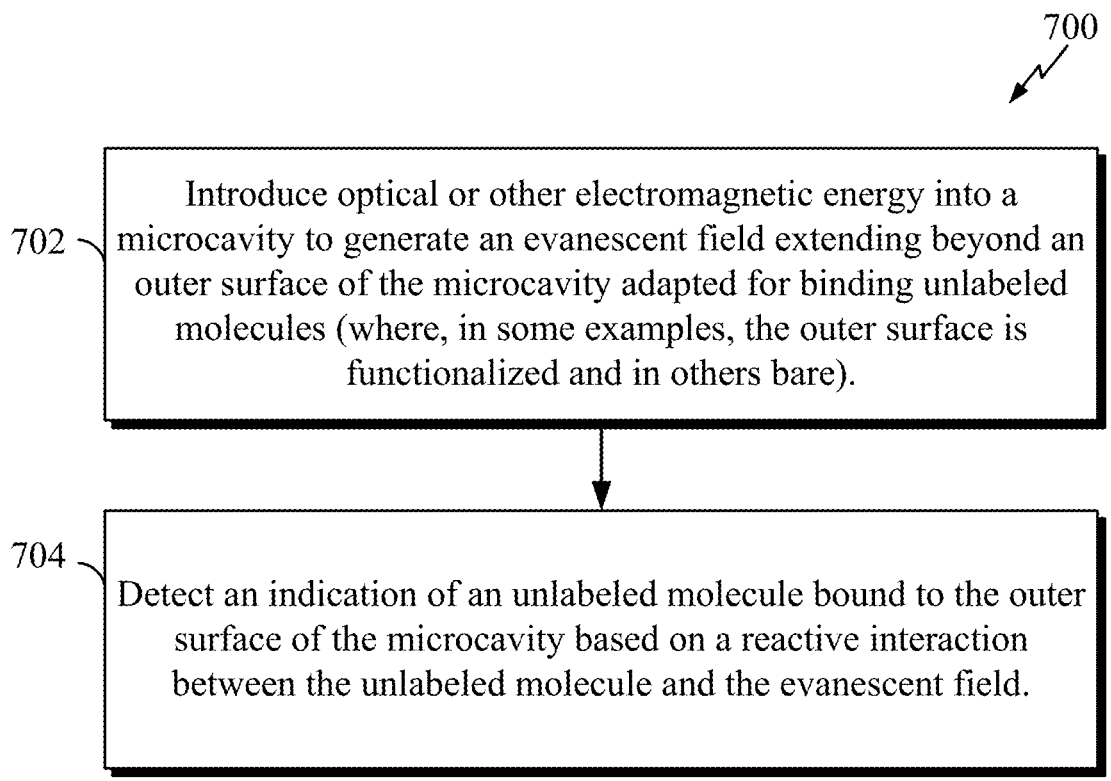
FIG. 7 provides an overview of alternative methods for detecting an indication of an unlabeled molecule using a microcavity.

FIG. 7 provides an overview of an exemplary method 700 for detecting an unlabeled molecule using a microcavity wherein frequency locking and balanced detection are not necessarily employed. Briefly, at 702, optical or other electromagnetic energy is introduced into a microcavity to generate an evanescent field extending beyond an outer surface of the microcavity adapted for binding unlabeled molecules (where, in some examples, the outer surface is functionalized and in others bare). At 704, an indication of an unlabeled molecule bound to the outer surface of the microcavity is detected based on a reactive interaction between the unlabeled molecule and the evanescent field. Hence, as shown in FIG. 7, frequency locking and balanced detection are not necessarily employed and at least some unlabeled molecules may be nevertheless detected, depending upon the SNR capabilities of the detection system. The technique of FIG. 7 may be implemented, for example, by modifying the system of FIG. 5 to replace the auto-balanced photoreceiver with a non-balanced detector and to omit the frequency-locking feedback.

Experimental Procedures and Results

Figure 8:
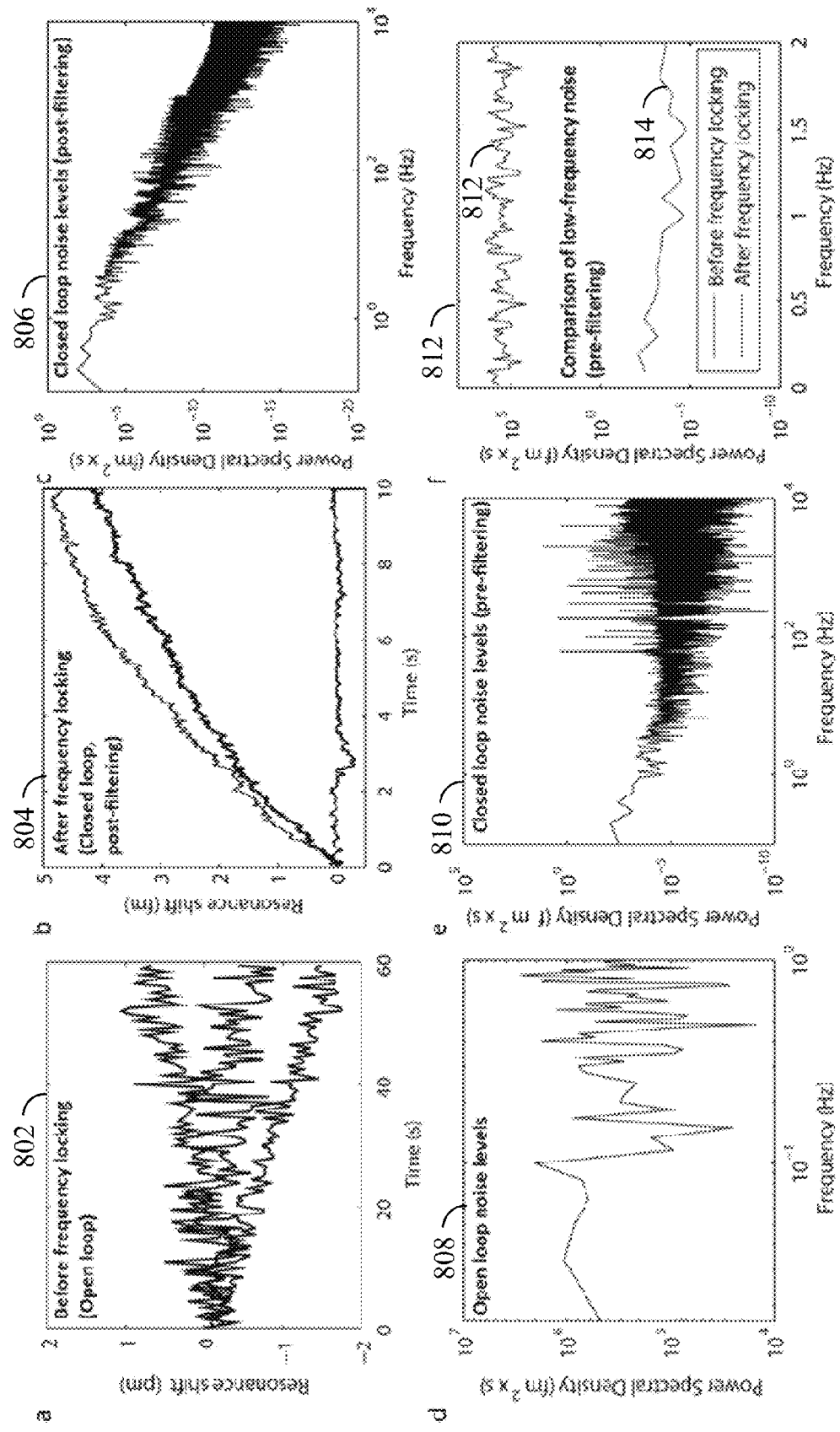
FIG. 8 provides graphs illustrating results for exemplary particle detection experiments.

FIG. 8 provides a set of graphs illustrating results for exemplary particle detection experiments performed with a TLB-6300 tunable diode laser (controller number: TLB-6300-LN) from Newport™ in combination with a DigiLock™ 110 from Toptica Photonics™. Top-of-peak locking was performed in auto-lock mode using a dither frequency of 2 kHz. The PID controller was set by Ziegler-Nichols tuning rules. The rise time of the system was determined to be 0.5 ms and the settling time 1.5 ms. Signals were detected using a Nirvana™ auto-balanced receiver (Model 2007) from Newport™. Polarization was adjusted using an in-line polarization controller from General Photonics™ (Product Number: PLC-003-S-90). Recombinant human interleukin-2 was obtained from Pierce Biotechnology™ (Product Number: R201520). Mouse IgG was obtained from Jackson ImmunoResearch™ (Code Number: 015-000-003). The microtoroid containing chip was affixed to stainless steel sample holder using double sided tape. A sample chamber was constructed on top of the sample holder by cantilevering a custom cut coverslip over a microscope slide spacer. Anti-CD81 used for the exosome experiments was obtained from Santa Cruz Biotechnology™. Prior to injection, particle containing solutions were thermally equilibrated for >1 hour in a 1 L room-temperature water bath. Solutions were then briefly (~2 seconds) vortexed and injected using a syringe pump (Harvard Apparatus™) and a 1 mL syringe fitted with a 23 gauge luer stub, tubing (ID 0.02 OD 0.06 WALL 0.02, VWR) and a small metal tube (Corp. 23 TW (0.025/0.0255 OD×0.0165/0.018 ID, New England Small Tubes™). After injection there was a 30 second delay before data recording. Data was recorded at 20 kHz using a 24-bit data acquisition card (NI-PCI-4461) from National Instruments™. Following data acquisition, Fourier filtering was performed to remove 60 Hz and its harmonics, 100 Hz, and 2 kHz. A median filter of window size 1001 was then applied.

As shown in FIG. 8, the combination of frequency locking feedback control and computational filtering reduces the noise level to $9.6 \times 10^{-4}$ fm over one-millisecond intervals where graph 802 (a) illustrates exemplary toroid response to a buffer (no suspended particles) solution before the implementation of frequency locking. The curves (n=3) show how the resonance wavelength of the toroid changes over time when immersed in a buffer solution. The microtoroid response shows large (~1 μm) fluctuations associated principally with scan-tracking, and an overall drift due to slight temperature changes which alter the microtoroid's index of refraction and radius (dλ/dT~ several picometers/° C.). The noise level (the root-mean-squared value) of the curve fluctuations is ~1 pm. Before computing the noise level, a computing device computationally removed the large thermal drift from the data by subtracting an exponential fit (not shown).

Graph 804 (b) illustrates exemplary toroid response to a buffer solution after the implementation of frequency locking and computational filtering. The noise level of the traces is $9.6 \times 10^{-4}$ fm over one-millisecond intervals and is much smaller than the noise level calculated from graph 802 before the addition of frequency locking feedback control. Sample was performed over a shorter time period in graph 804 (10 seconds vs. 60) as frequency locking allows sampling with a much greater frequency (20 kHz vs 100 Hz). Graph 806 (c) illustrates exemplary power spectrum of a data set in (b) after filtering (as shown in graph 808 (d)) of the power spectrum of a typical buffer data set before the addition of frequency locking feedback control. The magnitude of the y-axis provides a measure of the noise level of the FLOWER system which may be the limiting factor in sensitivity. Graph 810 (e) illustrates exemplary power spectrum of a typical buffer data set after the addition of feedback control, but before computational filters have been applied (i.e., the intrinsic noise of the system). The tallest peaks in the graph correspond to known noise sources and their harmonics. The mean noise level ($10^{-4}$ fm$^2$ s) is significantly less than the mean noise level ($10^5$ fm$^2$ s) seen in graph (c). Graph 812 (f) illustrates exemplary power spectra in (b) and (c) (here denoted 812 and 814) plotted on the same axes. The difference in mean noise levels is readily apparent, indicating the role of the feedback controller in quenching various noise mechanisms.

Figure 9:
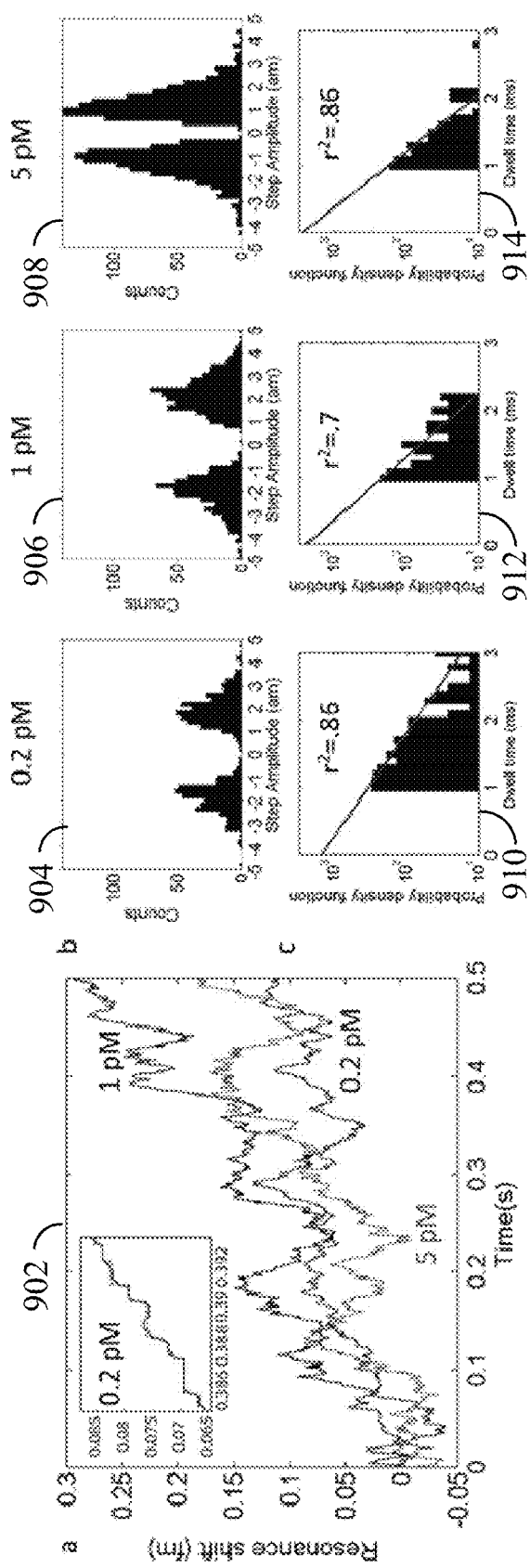
FIG. 9 provides graphs illustrating exemplary nanoparticle detection.

FIG. 9 provides a set of graphs illustrating individual 2.5 nm radius bead detection. A graph 902 (a) illustrates detection of 2.5 nm radius glass nanoparticles at different concentrations. Step down events represent the unbinding of particles. A zoom-in of the 0.2 pM case is shown in the inset of the graph. The data was filtered using a median filter and steps were fit (dashed line) using the step-fitting algorithm of Kerssemakers et al., cited above. A set of graphs 904, 906 and 908 (b) illustrates that, as expected, the mean step amplitude remains constant because the mean particle size does not change. A set of graphs 910, 912 and 914 (c) illustrates that the time in-between binding events (i.e. step duration) follows an exponential distribution, indicating that the binding of particles follows a Poisson process. As expected, this exponential distribution shifts to shorter times in a linear fashion with concentration, illustrated here in the log-linear plots as an increase in slope (r$^2$ indicates goodness of fit). In the histograms presented, dwell times faster than the digital low pass filter applied to the data (1 ms) were considered unreliable and were not included in the exponential fit. These results are consistent with single particle binding.

Figure 10:
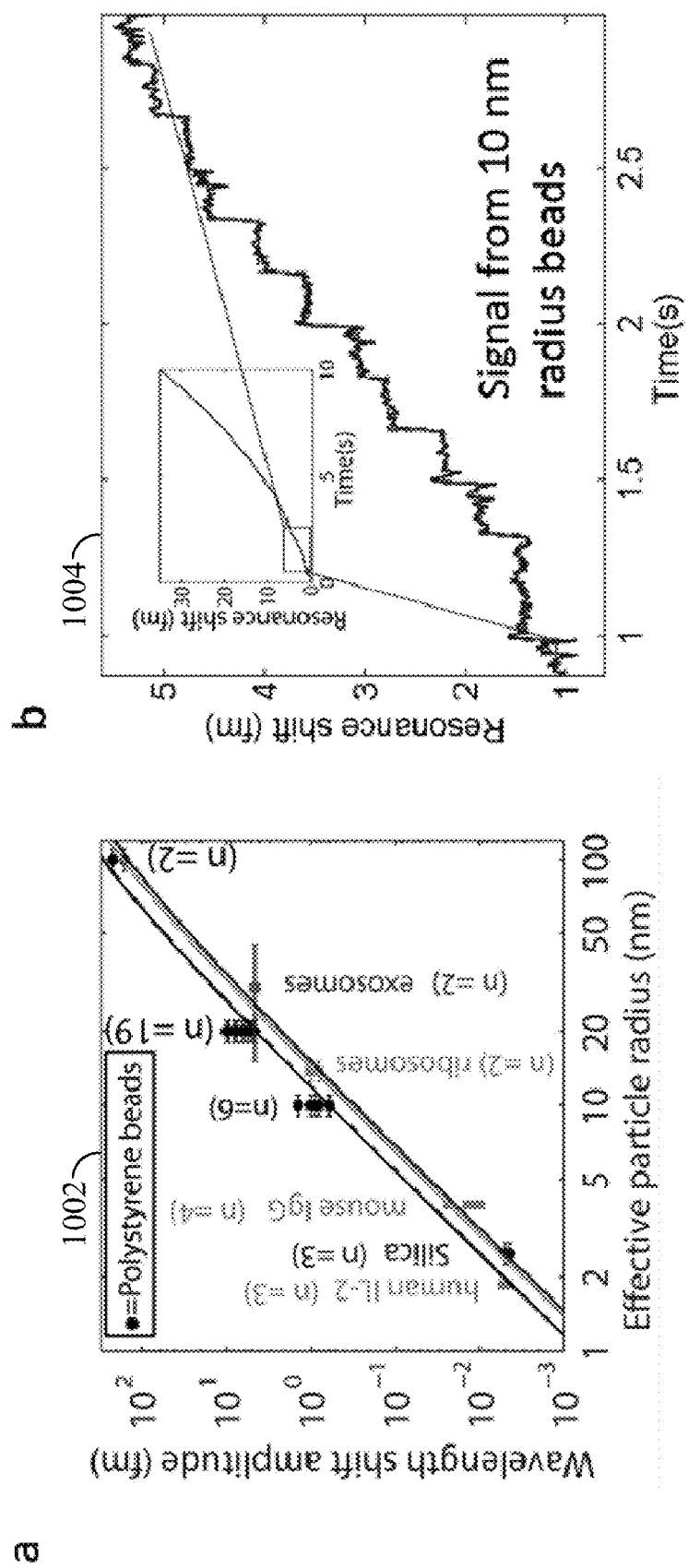
FIG. 10 provides graphs summarizing exemplary particle detection data.

FIG. 10 provides a pair of graphs summarizing the particle detection data. A graph 1002 (a) illustrates a wide range of particle sizes with radii from 2-100 nm were detected. For human IL-2 and mouse IgG, an effective particle radius was calculated based on spheres having the same molecular weights as the individual molecules. The solid lines are theoretical predictions based on the reactive sensing principle. Errors bars represent the known polydispersity of our samples. A graph 1004 (b) illustrates the resonance wavelength shift over time of the microtoroid as polystyrene latex nanoparticles 10 nm radius bind to the surface of the microtoroid. As a nanoparticle binds, the resonance frequency of the toroid changes. This change appears as a 'step' in the plot of resonance frequency shift over time. The step-fit is shown as a dashed line. The inset of the graph provides a zoom-out of the toroid response over the full recording range of 10 seconds. Additional data sets are discussed below.

Figure 11:
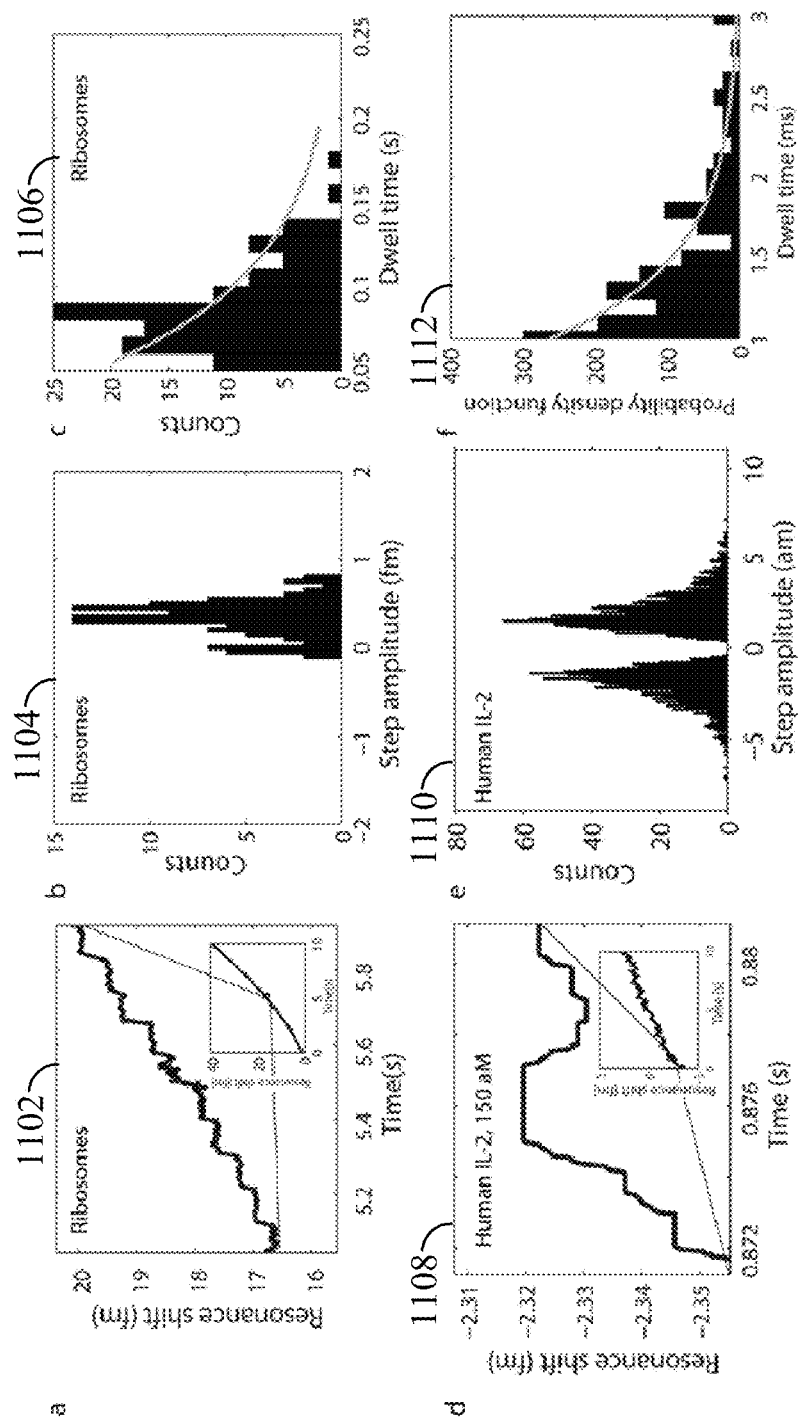
FIG. 11 provides graphs illustrating exemplary individual yeast ribosome and human interleukin-2 detection.

FIG. 11 provides a pair of graphs illustrating individual yeast ribosome (12.5 nm radius) and human interleukin-2 (2 nm radius) detection. A graph 1102 (a) illustrates the resonant wavelength shift over time of the microtoroid as ribosomes bind to the surface of the microtoroid and the step-fit. The inset of the graph provides a zoom-out of the toroid response over the full recording range of 10 seconds. A graph 1104 (b) illustrates a histogram of step amplitudes. The mean step amplitude of 0.39 fm corresponds to a size of 23 nm as predicted by the reactive sensing principle, thus suggesting that the binding of individual ribosomes are being observed. Negative step amplitudes correspond to unbinding events. A graph 1006 (c) illustrates a histogram of the time in between steps (dwell times). As expected for single-particle binding, the dwell time distribution follows an exponential fit. Graphs 1008, 1110 and 1112 (d, e, f) illustrate the same data as (a)-(c) but for IL-2 as opposed to ribosomes.

Thus, primary experimental results were presented and discussed in connection with FIGS. 8-11. In the following, further details regarding exemplary implementations are set forth.

Figure 12:
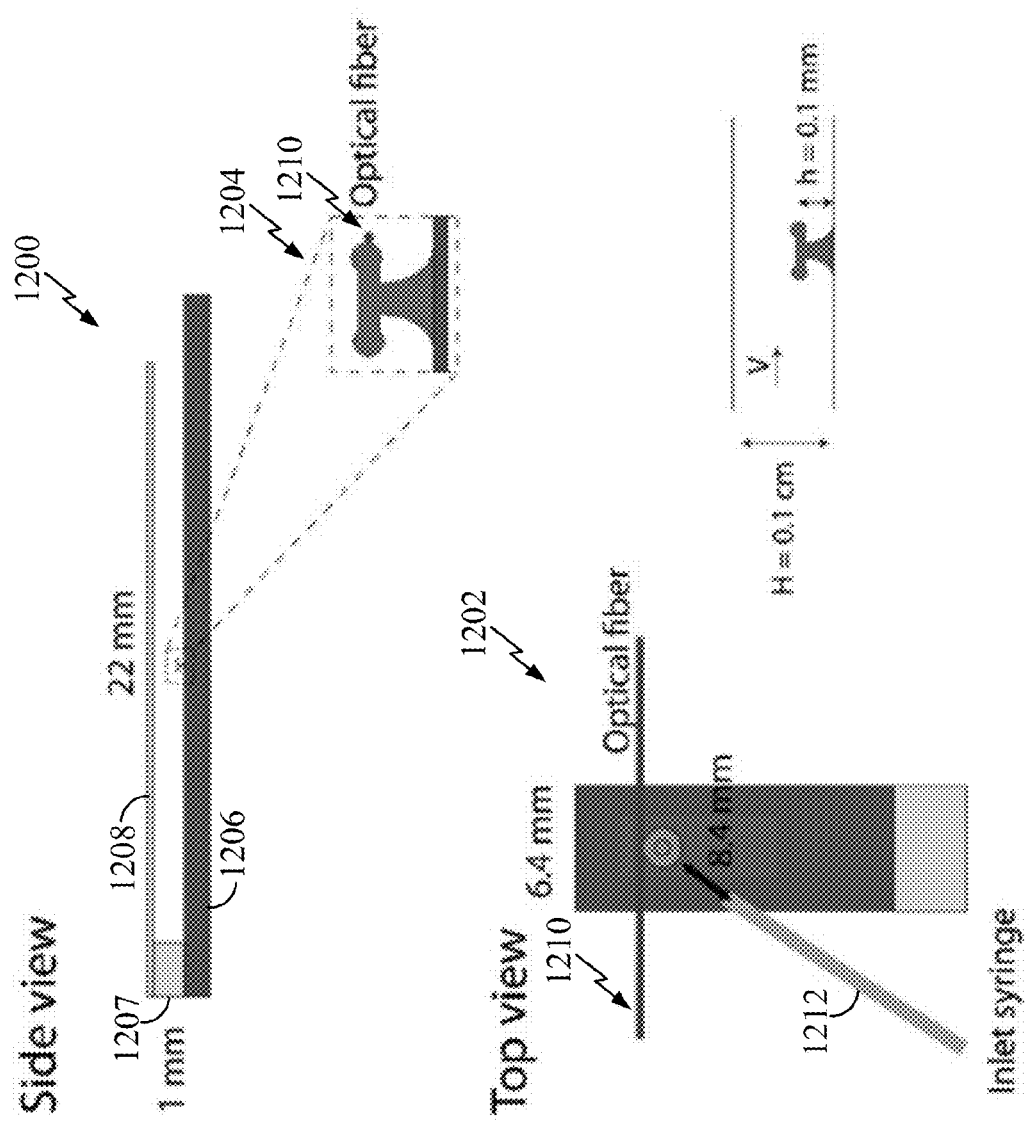
FIG. 12 provides views of a portion of an exemplary test setup.

FIG. 12 illustrates side 1200 and top 1202 views of a portion of a test setup with some exemplary dimensions. In this example, the microtoroid 1204 is mounted on a steel base 1206 and a glass coverslip 1208 is placed on top. A portion of a microscope slide 1207 may be used as a spacer. The sample chamber is left open to allow for an optical fiber 1210 to pass through. V is the injection velocity, h is the height of the microtoroid and H is the height of the sample chamber. The top view also shows an inlet syringe 1212. Note that the time in-between binding events is faster than from diffusion alone. In this regard, the arrival rate of particles to the vicinity of the toroid=$C\hat{Q}$, where C is the concentration (number of particles/volume), and $\hat{Q}$ is the injection flow rate (volume/time). Given a concentration of 150 aM and an injection rate of 1 mL/min, this gives an arrival rate of 1500 particles/second. The velocity, V, from injection is given by, V=$\hat{Q}$/A, where A is the cross-sectional area of the inlet tube. V is therefore 550 mm/s. From this one can calculate a Reynolds number of 550, meaning convection is 550 times bigger than viscous diffusion of the liquid molecules. The frequency, f, of vortex shedding over the toroid is given by f=V/h, where h=0.1 mm, therefore an encounter rate of $10^3$ to $10^4$ Hz is feasible. As smaller particles tend to be influenced by smaller vortices more, vortices shed from the ~500 nm diameter optical fiber may play a role, making the encounter rate even higher. However, the highly nonlinear flow process under stopped flow conditions is known to be complicated. A further analysis may resolve the mechanism of fast binding in small scale flow.

Insofar as noise determination is concerned, noise level can be established by measuring how the resonance wavelength of the microtoroid changes over time when it is immersed in a buffer (background) solution. Noise is calculated in this manner because the particle detection experiments are performed in buffer solutions, so measuring how the resonance wavelength of the microtoroid changes in just a buffer solution represents a control case of what the resonance shift looks like when there are no particles. One can calculate noise levels before and after feedback control by calculating the standard deviation of the resonance wavelength value after subtracting a general trend (discussed below). Before feedback control, the standard deviation of the resonance wavelength value over 60 seconds is ~1 pm. After enabling feedback control, the fluctuations are significantly decreased to ~0.07 fm over 10 seconds. (See, FIG. 8, discussed above.) The shorter time interval over which the signal is averaged in the frequency locking case reflects the higher data acquisition rate that is enabled with feedback control.

With the noise level (standard deviation) calculated over 1 ms intervals (which is the approximate time between binding events for r=2.5 nm nanoparticle experiments), this number reduces further to ~9.6×$10^{-4}$ fm. This represents an average over 20 data points for 10,000 intervals. It is noted that the noise level decreases when averaging over smaller time intervals as our noise is not white noise. Before these numbers are calculated, the data is computationally filtered to remove known sources of noise and then a median filter is applied of window size 1001. For example, using this method of calculating noise levels, along with measurements of maximum step size, the SNR for IL-2 in the experiment shown in graph 1108 of FIG. 11 is 5.2 and the SNR for the 10 nm radius nanoparticles (graph 1004 of FIG. 10) is 35.

A general trend can be subtracted from the buffer data before computing noise levels to account for thermal drift of the system. Due to the large circulating intensities within optical resonators, there is a significant, but slow (on the order of seconds), thermal drift of the resonance frequency over time. This is due to index of refraction changes due to temperature changes which have been established to be ~1 pm/1° C. in silica. Thermal drift may also occur due to temperature fluctuations in the room and is considered to be one of the main sources of environmental noise for optical resonators. One expects thermal drift in the absence of a temperature controlled environment and so it is reasonable to expect temperature changes of 1-2 degrees. A downward drift indicates cooling whereas an upwards drift indicates heating of the microtoroid. It is noted that this long term overall drift is large (>fm) compared to the wavelength shift expected from a single molecule which is 0.005 fm. In addition, it is also noted that the time scale of the long term shift due to temperature is on the order of seconds while the time scale of a single molecule binding event is on the order of milliseconds, and therefore, this thermal drift does not hamper the ability to detect individual binding events.

Figure 13:
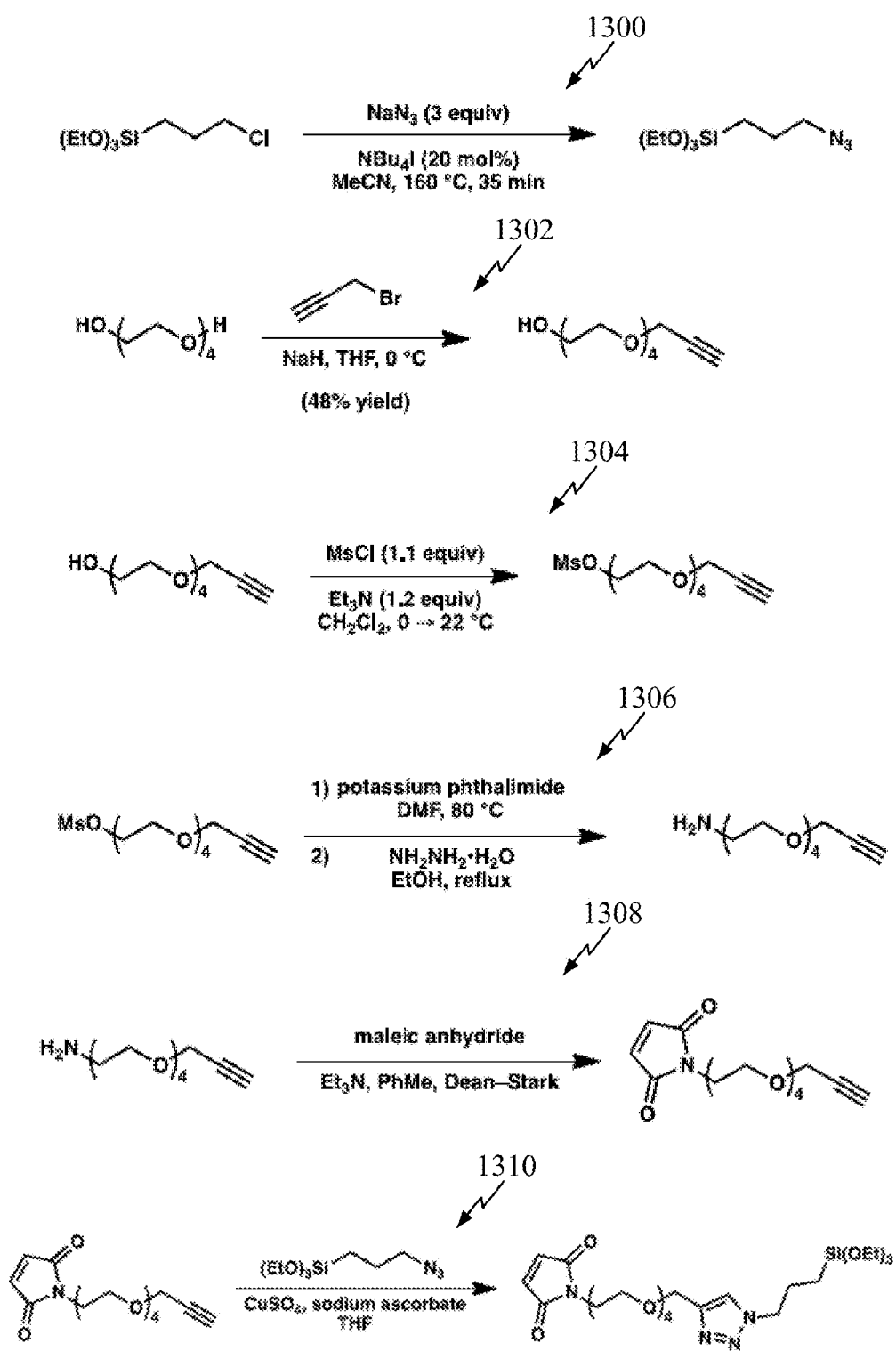
FIG. 13 illustrates various chemical formulas relevant to link synthesis.

FIG. 13 illustrates various chemical formulas relevant to link synthesis. Formula 1300 pertains to 3-azidopropyltriethoxysilane. Two flame-dried, 20 mL microwave vials were each charged with 3-chloropropyltriethoxysilane (1.0 mL, 4 mmol, 1 equiv), sodium azide (813.8 mg, 12 mmol, 3 equiv), tetrabutylammonium iodide (310.6 mg, 0.84 mmol, 0.2 equiv) and dry acetonitrile (20 mL). The vials were sequentially heated in a Biotage™ Initiator microwave (160° C.) for 35 minutes. The reaction mixtures were combined and the solvent was removed in vacuo. To the residue was added pentane, and the mixture was filtered through Celite then concentrated in vacuo. The crude product (1.5439 g, 75% yield) appeared clean by NMR, but could be further purified by Kugelrohr™ distillation (0.1-0.3 torr, 88° C. bath temperature) to afford a colorless oil: $^1$H NMR (300 MHz, CDCl$_3$) δ 3.82 (q, J=7.0 Hz, 4H), 3.27 (t, J=7.0 Hz, 2H), 1.79-1.64 (m, 2H), 1.23 (t, J=7.0 Hz, 9H), 0.75-0.60 (m, 2H).

Formula 1302 pertains to HO-TEG-Alkyne. A flame-dried 1 L round-bottom flask, equipped with a magnetic stir-bar was charged with sodium hydride (1.5070 g, 60% in mineral oil, 37 mmol, 1.2 equiv) then sealed with a rubber septum under nitrogen. To the flask was added THF (ca. 400 mL) via cannula, then the reaction mixture was cooled in an ice-water bath. Tetraethyleneglycol (8.0 mL, 46 mmol, 1.5 equiv) was added dropwise to afford a homogeneous mixture. To the stirring mixture was added propargyl bromide (3.4 mL, 80 wt % in toluene, 31 mmol, 1 equiv) dropwise, and the resulting solution was stirred until complete consumption of the bromide was observed by thin layer chromatography (2.5 hours). The reaction was quenched by addition of saturated ammonium chloride and water and the bulk of the THF was removed by rotary evaporation. The resulting mixture was extracted with dichloromethane (75 mL×4) and the combined organic fractions were dried over anhydrous magnesium sulfate, clarified with activated charcoal, filtered and concentrated in vacuo. The residue was purified by flash chromatography (20:1 DCM:MeOH) to afford the desired propargyl ether (3.5388 g, 48% yield): $^1$H NMR (300 MHz, CDCl$_3$) δ 4.20 (d, J=2.4 Hz, 2H), 3.75-3.63 (m, 14H), 3.63-3.58 (m, 2H), 2.65 (t, J=6.0 Hz, 1H), 2.42 (t, J=2.4 Hz, 1H).

Formula 1304 pertains to MsO-TEG-Alkyne. A flame-dried round-bottom flask was equipped with a magnetic stir-bar and charged with HO-TEG-Alkyne (3.4418 g, 14.8 mmol, 1 equiv). The flask was sealed with a rubber septum under nitrogen. To the flask was added dichloromethane (75 mL) and freshly distilled triethylamine (2.48 mL, 17.8 mmol, 1.2 equiv). The flask was then cooled in an ice-water bath, and mesyl chloride (1.26 mL, 16.3 mmol, 1.1 equiv) was added dropwise to the stirring mixture. Consumption of the starting material was observed by thin layer chromatography after 15 minutes, and saturated aqueous ammonium chloride was added then the phases were separated. The aqueous layer was extracted with additional dichloromethane (100 mL×3), then the combined organic layers were dried over magnesium sulfate, filtered, and concentrated in vacuo. The residue was purified by flash chromatography (40:1 DCM:MeOH) to afford the desired mesylate in a quantitative yield: $^1$H NMR (300 MHz, Chloroform-d) δ 4.43-4.33 (m, 2H), 4.20 (d, J=2.4 Hz, 2H), 3.81-3.73 (m, 2H), 3.73-3.60 (m, 12H), 3.08 (s, 3H), 2.43 (t, J=2.4 Hz, 1H).

Formula 1306 pertains to H$_2$N-TEG-Alkyne. A flame-dried 50 mL round-bottom flask was charged with MsO-TEG-Alkyne (1.0082 g, 3.2 mmol, 1 equiv) and sealed with a rubber septum under nitrogen. Dry DMF (13.5 mL) was added by syringe, followed by rapid addition of potassium phthalimide (720.8 mg, 3.9 mmol, 1.2 equiv). The thick slurry was heated in an 80° C. oil bath with good stirring. After 3 hours, additional potassium phthalimide (380 mg, 2.0 mmol) was added to the mixture, and heating was continued overnight. The reaction mixture was partitioned between dichloromethane and water and the phases were separated. The aqueous layer was extracted exhaustively with dichloromethane (until no product remained in the aqueous layer). The combined organics were dried over magnesium sulfate, filtered and concentrated in vacuo. The residue was purified by flash chromatography (40:1 DCM:MeOH) to afford a white crystalline solid that was carried forward in its entirety to the next stage. A round-bottom flask was charged with the phthalimide product from the previous stage, hydrazine hydrate (473 µL, 9.74 mmol, 3 equiv), and absolute ethanol (32 mL). The flask was equipped with a stir bar and a reflux condenser. The mixture was heated to reflux with stirring for an hour, at which point complete consumption of the starting material was observed by thin layer chromatography. The reaction mixture was filtered to remove the white precipitate formed in the reaction and the filtrate was concentrated in vacuo. The residue was dry-loaded onto silica gel and purified by column chromatography (40:1 DCM:MeOH→15:1:0.05 DCM:MeOH:NH$_4$OH$_{(aq)}$→10:1:0.05 DCM:MeOH:NH$_4$OH$_{(aq)}$) to afford the primary amine (616.0 mg, 82% yield over two steps) as a yellowish oil: $^1$H NMR (300 MHz, CDCl$_3$) δ 4.23-4.12 (m, 2H), 3.75-3.56 (m, 14H), 3.55-3.44 (m, 2H), 2.91-2.79 (m, 2H), 2.46-2.39 (m, 1H), 1.84 (s, 2H).

Formula 1308 pertains to MAL-TEG-Alkyne. A round-bottom flask was charged with H$_2$N-TEG-Alkyne (231 mg, 1 mmol, 1 equiv), maleic anhydride (107.7 mg, 6.5 mmol, 1.1 equiv), triethylamine (14 µL, 0.1 mmol, 0.1 equiv), and toluene (30 mL). The flask was fitted with a Dean-Stark trap and a reflux condenser, then heated to vigorous reflux for 36 h. The reaction mixture was concentrated in vacuo and dissolved in dichloromethane (60 mL). This solution was washed with aqueous hydrochloric acid (0.1 N) then brine. The organic layer was dried over anhydrous magnesium sulfate, filtered, and concentrated in vacuo. The residue was purified by column chromatography (40:1 DCM:MeOH) to afford the maleimide (42.0 mg, 14% yield): $^1$H NMR (300 MHz, CDCl$_3$) δ 6.70 (s, 2H), 4.20 (d, J=2.4 Hz, 2H), 3.76-3.58 (m, 16H), 2.43 (t, J=2.4 Hz, 1H), 1.62 (s, 2H).

Formula 1310 pertains to MAL-TEG-Si. A 4 mL vial was charged with MAL-TEG-Alkyne (35.0 mg, 0.11 mmol, 1 equiv) and THF (1 mL). To the solution was added 3-azidopropyltriethoxysilane (27.8 mg, 0.11 mmol. 1 equiv) and sodium ascorbate (13.4 mg, 0.068 mmol, 0.5 equiv). Finally, copper (II) sulfate (11 µL, 1M in H$_2$O, 0.011 mmol, 0.1 equiv) was added and a brown precipitate was immediately observed. After 30 minutes, additional copper (II) sulfate (22 µL) was added, and the suspension was stirred overnight. The reaction mixture was partitioned between dichloromethane and brine, and the phases were separated. The aqueous phase was further extracted with dichloromethane (15 mL×3). The combined organics were dried over magnesium sulfate, filtered and concentrated in vacuo. The residue was purified by flash chromatography (20:1 DCM:MeOH) to afford the desired triazole (39.4 mg, 63% yield): $^1$H NMR (300 MHz, CDCl$_3$) δ 7.56 (s, 1H), 6.67 (s, 2H), 4.65 (s, 2H), 4.31 (t, J=7.2 Hz, 2H), 3.78 (q, J=7.0 Hz, 6H), 3.71-3.51 (m, 16H), 2.07-1.91 (m, 2H), 1.18 (t, J=7.0 Hz, 9H), 0.64-0.50 (m, 2H).

Figure 14:
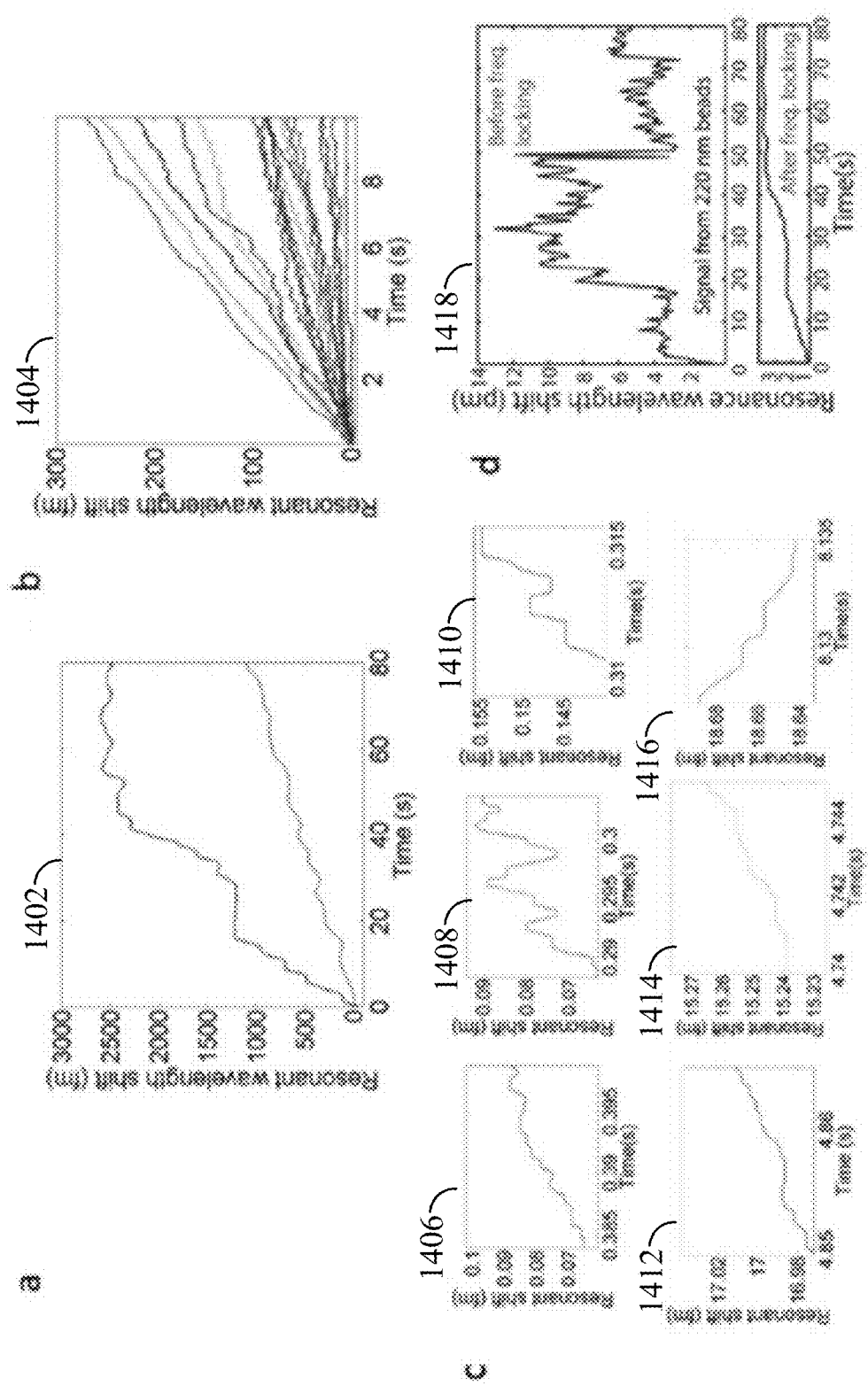
FIG. 14 provides graphs illustrating exemplary nanoparticle detection data for 5, 40, and 200 nanometer (nm) diameter nanoparticles.

FIG. 14 provides a set of graphs illustrating nanoparticle detection data for 5, 40, and 200 nm diameter nanoparticles. Additional 20 nm nanoparticle data is shown in graph 1402 (a), which provides a zoom-in of resonant wavelength shift over time of the microtoroid as 200 nm polystyrene latex nanoparticles bind to the surface of the microtoroid. Each trace represents an experiment performed on a different toroid. Graph 1404 (b) provides a zoom-in of resonant wavelength shift over time of the microtoroid as 40 nm polystyrene latex nanoparticles bind to the surface of the microtoroid. The data presented here is of repeated injections on the same toroid. Two data points represent a repeated injection on a second toroid as shown in graphs 1406-1416 (c), which provide a zoom-in of resonant wavelength shift over time of the microtoroid as 5 nm glass nanoparticles bind to the surface of the microtoroid. This represents data from two different toroids. The top portion of graph 1418 (d) illustrates a signal from a 220 nm nanoparticle solution without frequency locking has a noise level higher than signal. The apparent steps in this trace are too large to be single 220 nm nanoparticle, and are likely experimental or electronic noise. The bottom portion of the figure illustrates data for the 200 nm nanoparticle detection experiment performed using frequency locking. The noise is essentially invisible when plotted on the same axis scale.

Figure 15:
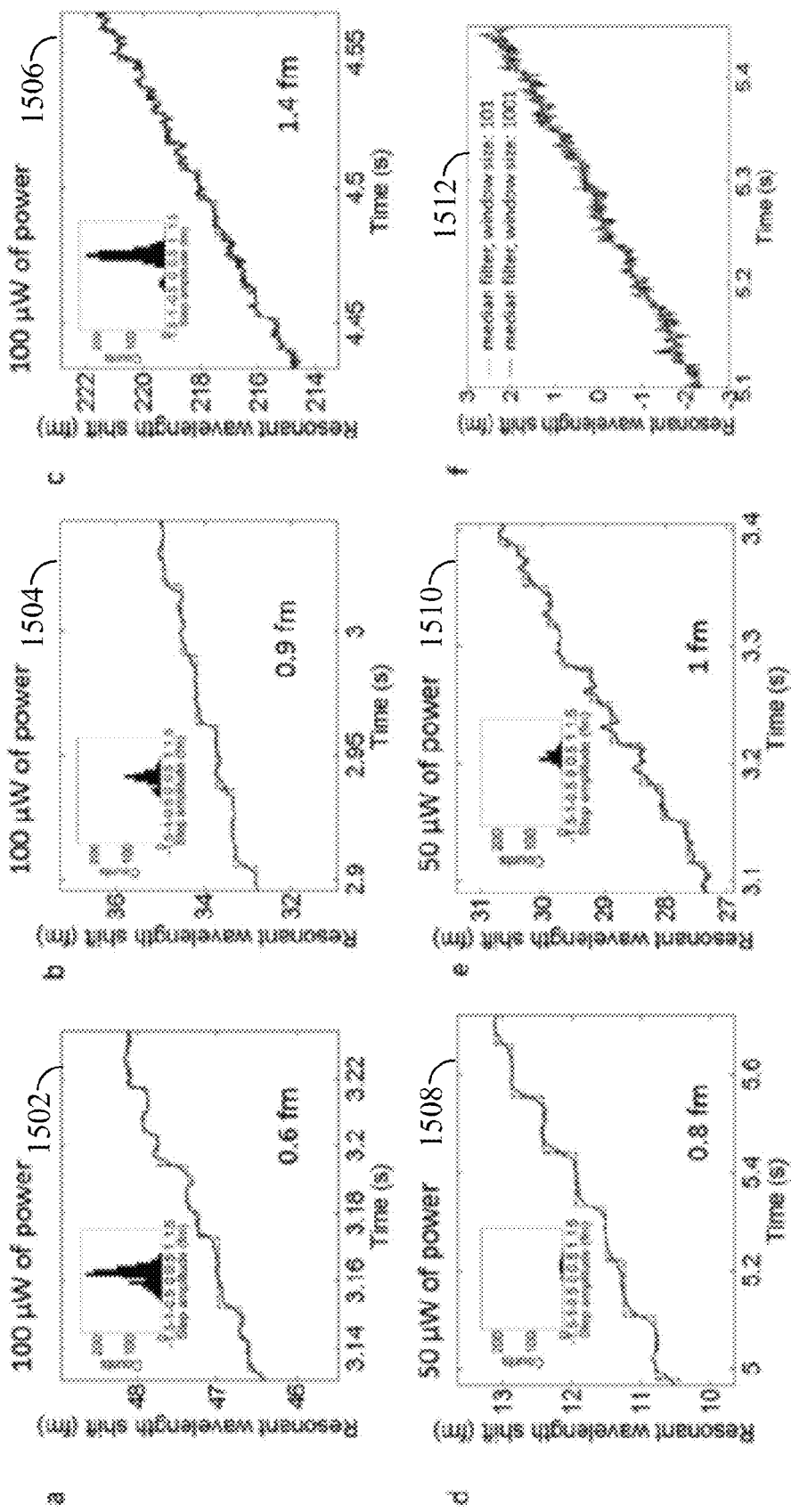
FIG. 15 provides graphs illustrating exemplary nanoparticle detection data for 20 nm nanoparticles at different input coupling powers.

FIG. 15 provides a set of graphs illustrating nanoparticle detection data for 20 nm nanoparticle detection by the microtoroid at different input coupling powers shows no detectable difference in step amplitude. Graphs 1502-1506 (a)-(c) provide a zoom-in of 20 nm nanoparticle detection experiments performed at 100 µW of input power. The resonant wavelength shift over time of the microtoroid as the nanoparticles bind to the surface of microtoroid is shown as a solid line. The step-fit is shown as a dashed line. The insets show histograms of the step amplitude. The maximum step amplitude is reported in the lower right hand corner of each graph. Graphs 1508-15012 (d)-(e) provide a zoom-in of 20 nm nanoparticle detection experiments performed at 50 µW of input power. The resonant wavelength shift over time of the microtoroid as the nanoparticles bind to the surface of the microtoroid is shown in solid lines. The step-fit is shown as a dashed line. The insets show histograms of the step amplitude. No observable difference in step amplitude was noticed between the two different powers. For consistency, a median filter window size of 1001 was used in all experiments throughout the paper, however, for visualization purposes in graphs (a), (b), (c), and (e), median window filter sizes of 101, 101, 101, and 11, respectively were chosen. This does not significantly alter found step heights and locations but was done because for these specific cases due to differences in arrival times of the nanoparticles, a median widow size of 1001 tends creates an overly rounded step-appearance. Graph 1512 (f) illustrates data from (e), plotted with a median window filter size of 101 and a median window filter size of 1001. Increasing the median window filter size to 1001 does not alter the step height and location, but creates an overly rounded appearance. These experiments were performed on the same microtoroid.

Figure 16:
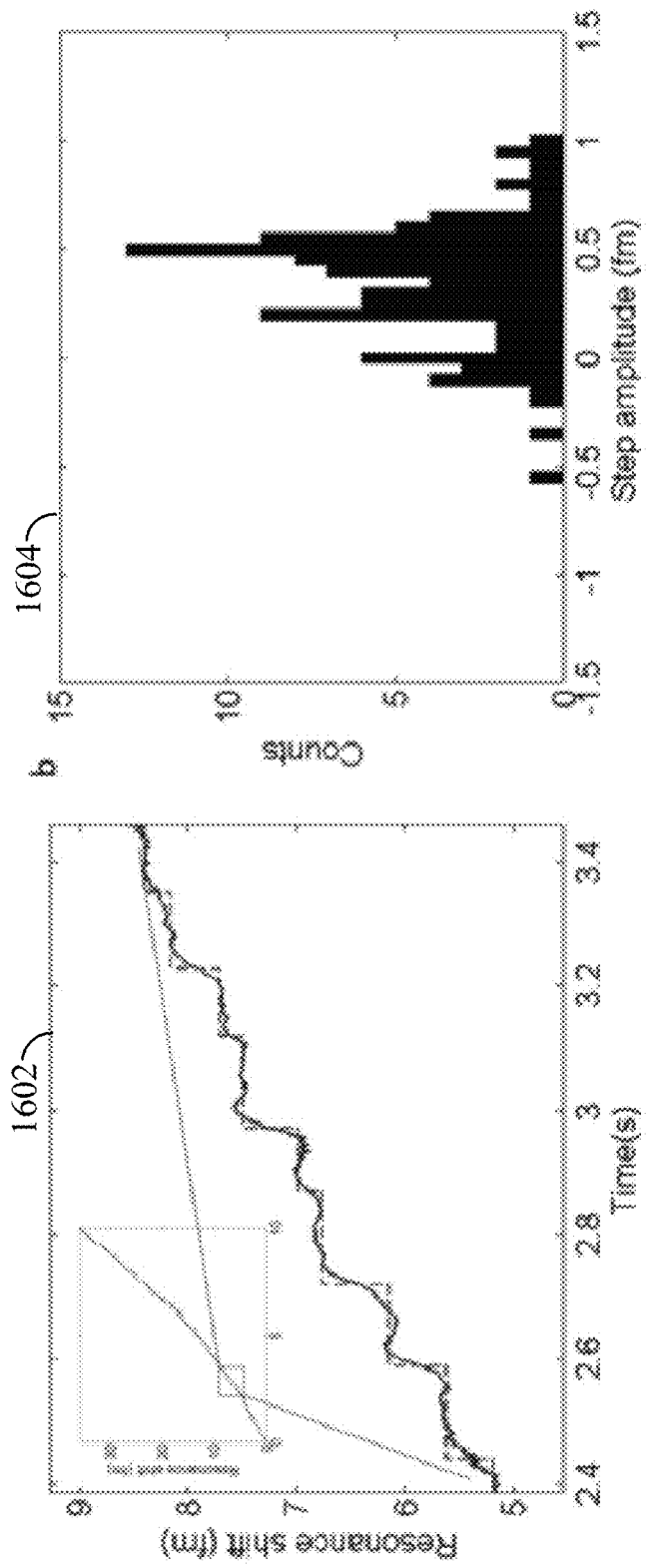
FIG. 16 provides graphs illustrating exemplary yeast ribosome detection.

FIG. 16 provides a pair of graphs illustrating individual yeast ribosome (~25 nm) detection. Graph 1602 (a) provides zoom in of the resonant wavelength shift over time of the microtoroid as ribosomes bind to the surface of the microtoroid. The step-fit is shown superimposed as a dashed line. This is a similar but different data set than is shown in FIG. 11. The inset of graph 1602 provides a zoom-out of the toroid response over the full recording range of 10 seconds. Graph 1604 (b) provides a histogram of step amplitudes. The mean step amplitude of ~0.35 fm is similar to the value shown in FIG. 11 (~0.39 fm). A step amplitude of ~0.35 fm corresponds to a particle diameter of 22 nm as predicted by our nanoparticle data thus suggesting that the binding of individual ribosomes is being observed.

Figure 17:
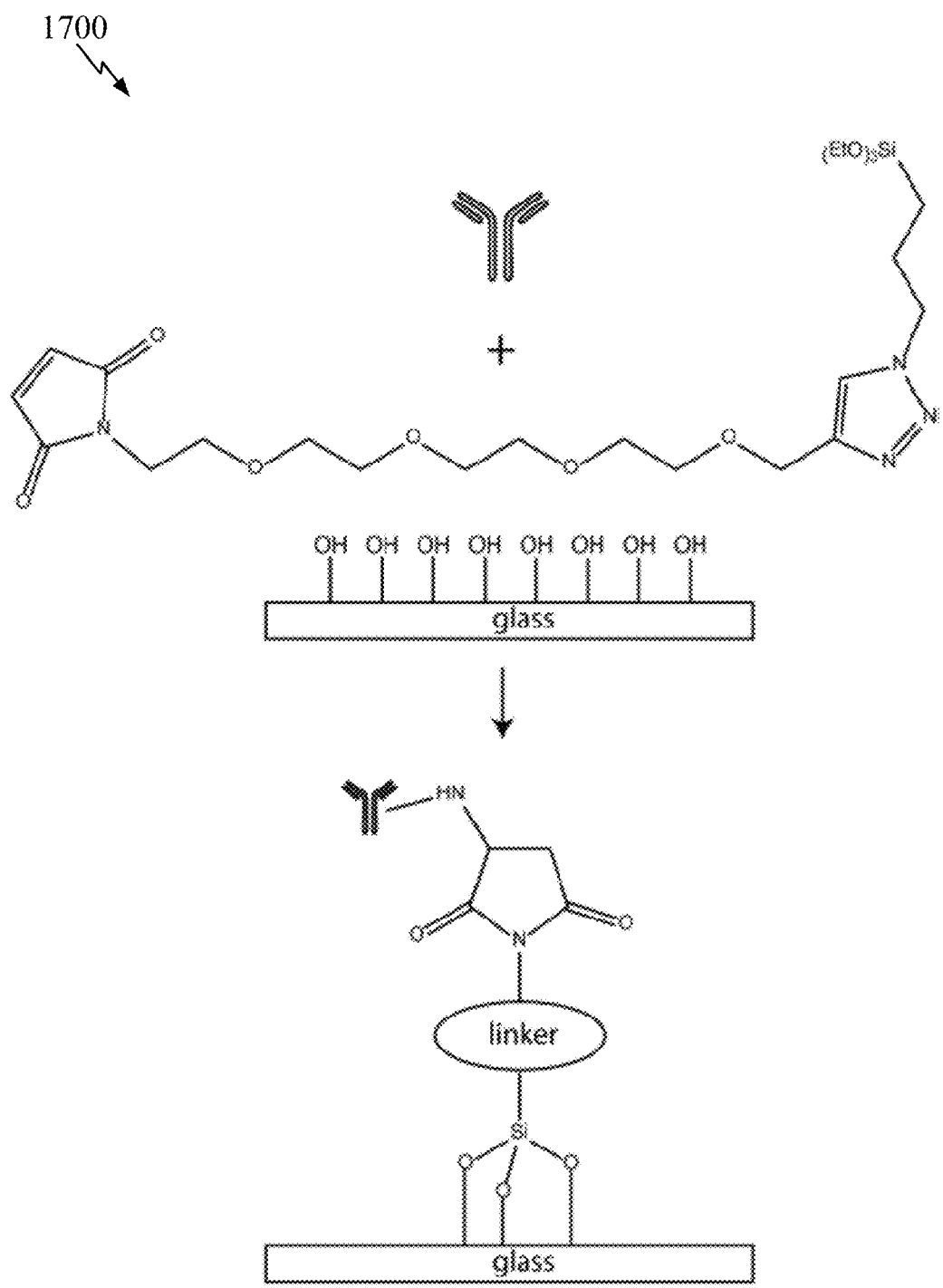
FIG. 17 provides a schematic illustration of exemplary microtoroid sensitization for biological detection.

FIG. 17 provides a schematic illustration 1700 of how the surface of the toroid may be sensitized for biological detection. A silane-PEG-maleimide linker is covalently bound to the surface of the toroid (represented in FIG. 17 as a glass substrate). Antibodies bind to the maleimide portion of the linker allowing for the selective detection of biological elements.

Figure 18:
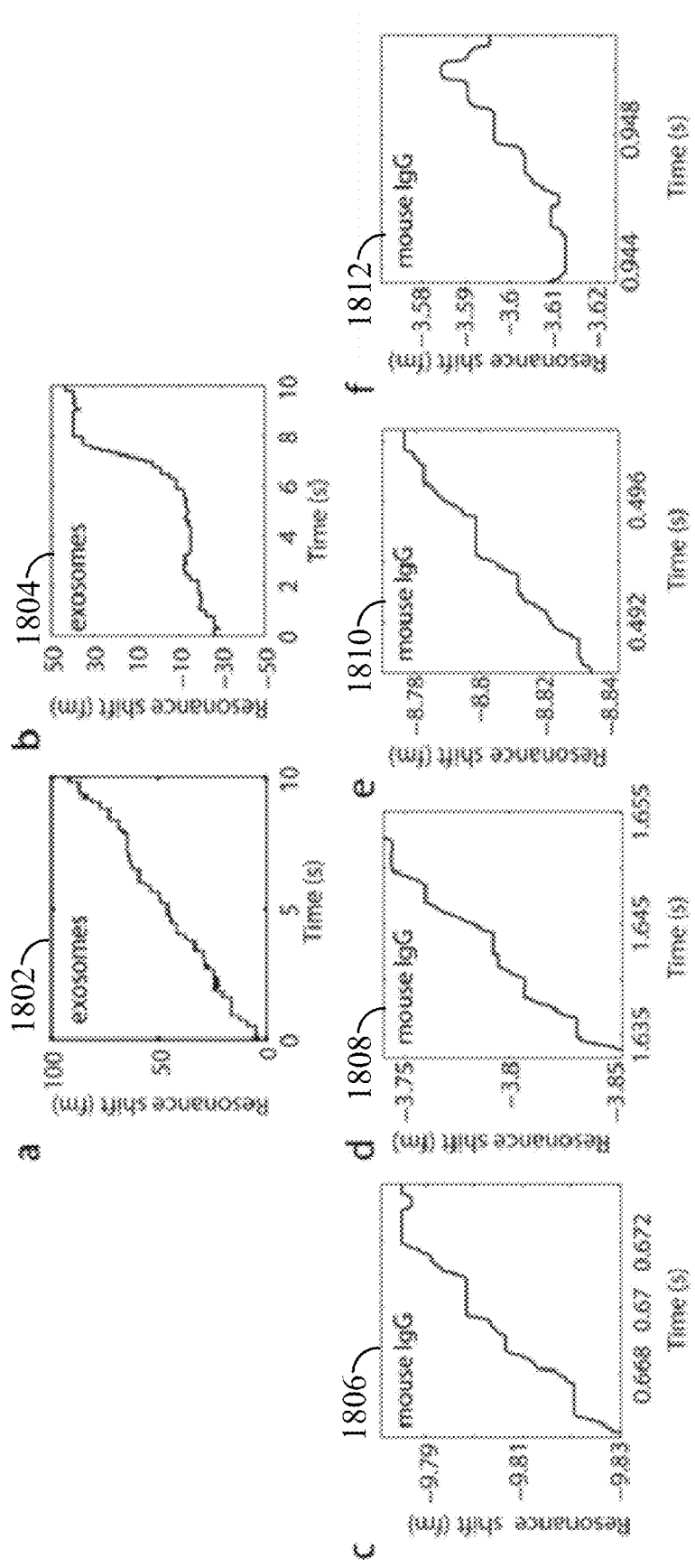
FIG. 18 provides graphs illustrating exemplary exosome and mouse IgG bioparticle detection data.

FIG. 18 provides a set of graphs illustrating exosome and mouse IgG bioparticle detection data. Graphs 1802 and 1804 (a)-(b) show exosome detection recorded from two different experiments. As exosomes bind to the surface of the microtoroid, the resonant wavelength of the microtoroid shifts as shown. Toroids were functionalized with the antibody CD-81. Graphs 1806-1812 (c)-(f) provide a zoom-in of Mouse IgG detection data from four different experiments. As expected, the step amplitudes for the IgG detection are much smaller than for the exosome detection.

Figure 19:
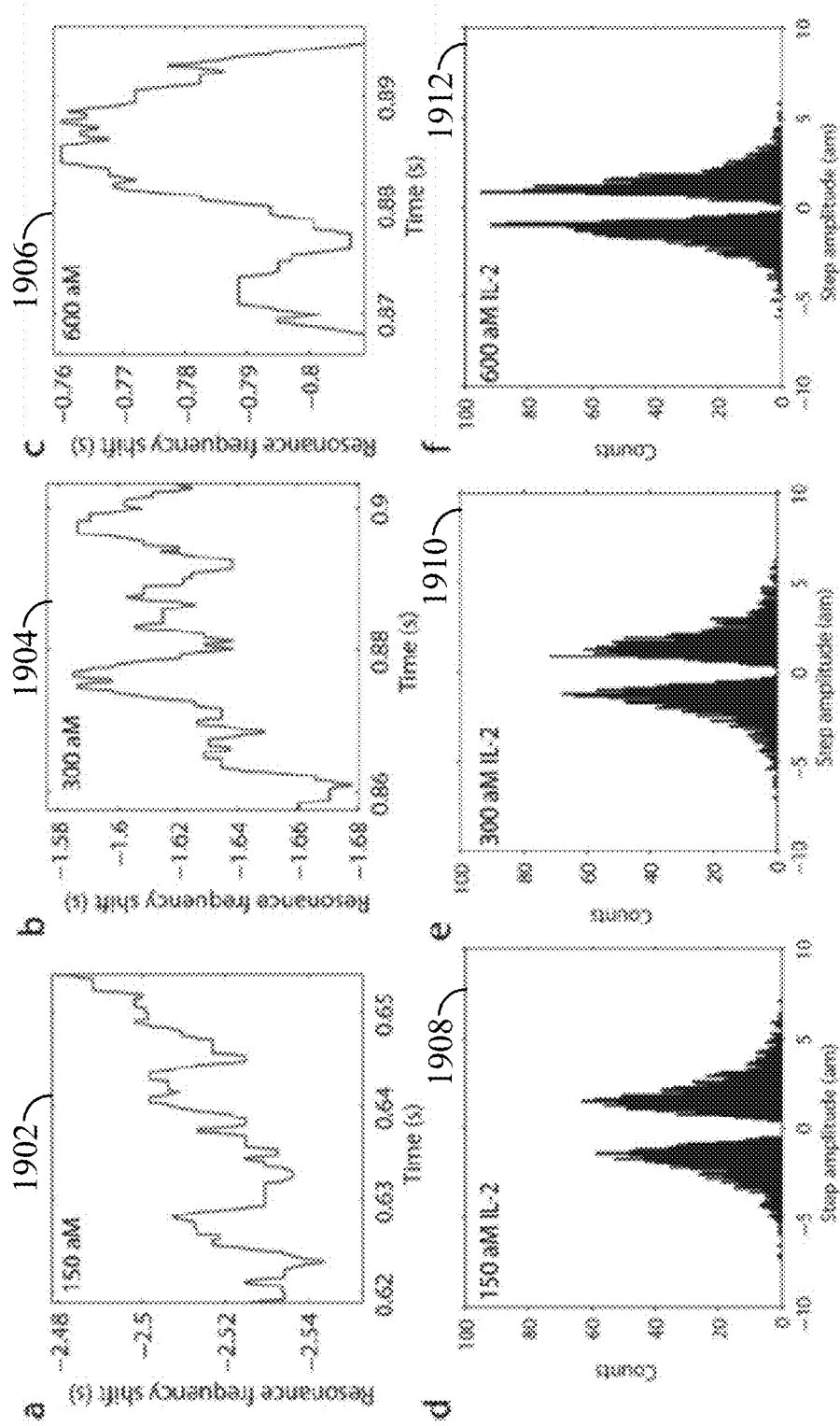
FIG. 19 provides a set of graphs illustrating exemplary IL-2 detection data at three different concentrations.

FIG. 19 provides a set of graphs illustrating IL-2 detection data at three different concentrations. Graphs 1902-1906 (a)-(c) provide zoom-in illustrations of IL-2 step traces. Traces show the resonance wavelength shift over time of the microtoroid as molecules bind to the surface of the microtoroid. Graphs 1908-1912 (d)-(f) provide corresponding step amplitude histograms. As the concentration increases, the total number of particles increases in a linear fashion.

Insofar as theory is concerned, the wavelength shift upon particle binding can depend on where on the resonator the particle lands. The wavelength shift may be represented as:

$$(\Delta\lambda)_{max} = \frac{Da^3 [E_0^2(r_e)/E_{max}^2]}{2V_m}\lambda, \quad (1)$$

The largest wavelength shift ($\Delta\lambda_{max}$) occurs for particles binding at the equator of the microtoroid where the electric field is the largest. The amplitude of this shift is related to the size of the radius (a) of the bound particle through Eq. (1). In Equation (1), D is a dielectric factor calculated from the index of refraction of the particle and its surrounding media, $\lambda$ is the wavelength of the laser, $V_m$ is the volume of the electromagnetic field (mode) within the toroid, and $E_0^2(r_e)/E^2_{max}$ represents the ratio of the intensity at the toroid surface where the particle binds over the maximum intensity within the cavity. Both $V_m$ and $E_0^2(r_e)/E^2_{max}$ are calculated from finite element simulations (not shown herein) and are found to be 330 $\mu m^3$ and 1/5.5, respectively.

The various features of the invention described herein can be implemented in different systems without departing from the invention. It should be noted that the foregoing embodiments are merely examples and are not to be construed as limiting the invention. The description of the embodiments is intended to be illustrative, and not to limit the scope of the claims. As such, the present teachings can be readily applied to other types of methods and apparatus and many alternatives, modifications, and variations will be apparent to those skilled in the art. Note also that the term "including" as used herein is intended to be inclusive, i.e. "including but not limited to."

What is claimed is:

1. A method for particle detection, comprising:
    introducing electromagnetic energy into a microcavity to generate an evanescent field extending beyond an outer surface of the microcavity; and
    detecting an indication of a particle bound to the outer surface of the microcavity based on a reactive interaction between the particle and the evanescent field using frequency locking and balanced detection.

2. The method of claim 1 wherein the particle comprises a plurality of unlabeled molecules.

3. The method of claim 1 wherein the particle is a single unlabeled molecule.

4. The method of claim 1 wherein the particle comprises one or more nanoparticles.

5. The method of claim 1 wherein the electromagnetic energy comprises optical energy received from a coherent light source.

6. The method of claim 5 wherein introducing energy comprises coupling optical energy into the microcavity from a waveguide to circulate optical energy inside the microcavity to generate an evanescent field of sufficient strength to react with one or more of the particles to cause a detectable shift in a wavelength of optical energy resonating in the microcavity.

7. The method of claim 6 further comprises splitting optical energy from the coherent light source onto first and second waveguide arms to couple a first portion of the optical energy into the microcavity using the first arm of the waveguide while routing a second portion of the optical energy along the second arm of the waveguide without microcavity coupling.

8. The method of claim 7 further comprising a balanced receiver to receive optical energy along the first and second arms of the waveguide wherein detecting an indication of a particle using balanced detection comprises generating a balanced difference signal using the balanced receiver wherein the difference signal is representative of a peak resonance wavelength associated with one or more particles.

9. The method of claim 8 further comprising frequency-locking system to receive an output of the balanced receiver wherein detecting an indication of a particle using frequency locking comprises locking a frequency of the coherent light source to a frequency corresponding to the peak resonance wavelength associated with one or more of the particles.

10. The method of claim 6 wherein the waveguide comprises an optical fiber coupled directly to the microcavity to provide over-coupling.

11. The method of claim 1 wherein detecting an indication of a particle based on the reactive interaction between the particle and the evanescent field using frequency locking and balanced detection improves a signal-to-noise ratio associated with the detection.

12. The method of claim 1 wherein detecting an indication of the particle based on the reactive interaction between the particle and the evanescent field further employs digital filtering including one or more of Fourier filtering and median filtering.

13. The method of claim 1 wherein the microcavity is a microtoroid.

14. The method of claim 13 wherein the microtoroid is planar and formed of silica.

15. The method of claim 1, wherein the microcavity is immersed in an aqueous environment during detection of the indication of the particle.

16. The method of claim 1, wherein the microcavity has a Q value sufficient to allow detection of individual unlabeled molecules bound to the outer surface based on a wavelength shift of optical energy resonating in the microcavity.

17. The method of claim 16, wherein the microcavity has a Q value less than $10^6$.

18. The method of claim 1, wherein the outer surface is functionalized with one or more of a chemically active substance, a biologically active substance, an antibody, an antigen and a protein.

19. A system for particle detection, comprising:
an input system operative to introduce electromagnetic energy into a microcavity to generate an evanescent field extending beyond an outer surface of the microcavity; and
a frequency-locked and balanced detector operative to detect an indication of a particle bound to the outer surface of the microcavity based on a reactive interaction between the particle and the evanescent field using frequency locking and balanced detection.

20. A method for unlabeled molecule detection, comprising:
introducing electromagnetic energy into a microcavity to generate an evanescent field extending beyond an outer surface of the microcavity; and
detecting an indication of an unlabeled molecule bound to the outer surface of the microcavity based on a shift in wavelength of the electromagnetic energy resonating in the microcavity due to a change in effective path length in a reactive interaction between the unlabeled molecule and the evanescent field that is independent of the optical power of the electromagnetic energy.

* * * * *